(12) United States Patent
Riegel et al.

(10) Patent No.: US 8,846,565 B2
(45) Date of Patent: Sep. 30, 2014

(54) WATER-ABSORBING POLYMERIC PARTICLES AND METHOD FOR THE PRODUCTION THEREOF

(75) Inventors: Ulrich Riegel, Landstuhl (DE); Thomas Daniel, Waldsee (DE); Dieter Hermeling, Böhl-Iggelheim (DE); Mark Elliott, Ludwigshafen (DE); Stefan Bruhns, Mannheim (DE)

(73) Assignee: BASF SE, Ludwigshafen (DE)

( * ) Notice: Subject to any disclaimer, the term of this patent is extended or adjusted under 35 U.S.C. 154(b) by 478 days.

(21) Appl. No.: 12/668,183

(22) PCT Filed: Jul. 21, 2008

(86) PCT No.: PCT/EP2008/059496
§ 371 (c)(1),
(2), (4) Date: Jan. 7, 2010

(87) PCT Pub. No.: WO2009/016055
PCT Pub. Date: Feb. 5, 2009

(65) Prior Publication Data
US 2010/0184594 A1      Jul. 22, 2010

(30) Foreign Application Priority Data
Jul. 27, 2007   (EP) ..................................... 07113326

(51) Int. Cl.
*B01J 20/26*   (2006.01)
*B01J 20/22*   (2006.01)
*A61L 15/60*   (2006.01)
*A61L 15/42*   (2006.01)
*A61L 15/58*   (2006.01)

(52) U.S. Cl.
CPC .................. *A61L 15/60* (2013.01); *A61L 15/42* (2013.01); *A61L 15/58* (2013.01)
USPC ............................ 502/402; 502/400; 502/401

(58) Field of Classification Search
USPC .......................... 502/400, 401, 402, 403, 404
See application file for complete search history.

(56) References Cited

U.S. PATENT DOCUMENTS

| 4,043,952 A | 8/1977 | Ganslaw et al. |
| 5,599,335 A | 2/1997 | Goldman et al. |

(Continued)

FOREIGN PATENT DOCUMENTS

| WO | WO-9526209 A1 | 10/1995 |
| WO | WO-2004024816 | 3/2004 |

(Continued)

OTHER PUBLICATIONS

International Search Report in PCT/EP2008/059495 dated Jun. 17, 2009.

*Primary Examiner* — Stanley Silverman
*Assistant Examiner* — Daniel Berns
(74) *Attorney, Agent, or Firm* — Marshall, Gerstein & Borun LLP

(57) ABSTRACT

The present invention relates to a water absorbing material obtainable by a process comprising the steps of bringing particles of a non surface-crosslinked water-absorbing polymer in contact with
a) at least one postcrosslinker,
b) 10-1000 ppm, based on the non surface-crosslinked water-absorbing polymer, of at least one Nitrogen-containing water-soluble polymer of which the Nitrogen can be protonated, and
c) at least one hydrophobic polymer
and heat-treating the particles thus obtained at a temperature in the range from 120° C. to 300° C. and a method for the production thereof.

12 Claims, 3 Drawing Sheets

(56) References Cited

U.S. PATENT DOCUMENTS

| | | |
|---|---|---|
| 5,731,365 A | 3/1998 | Engelhardt et al. |
| 6,395,830 B1 * | 5/2002 | Jonas et al. ............. 525/102 |
| 2007/0197111 A1 | 8/2007 | Dieleman et al. |
| 2008/0125533 A1 | 5/2008 | Riegel et al. |

FOREIGN PATENT DOCUMENTS

| | | |
|---|---|---|
| WO | WO-2004069293 | 8/2004 |
| WO | WO-2004069404 | 8/2004 |
| WO | WO-2004069915 | 8/2004 |
| WO | WO-2005044900 A1 | 5/2005 |
| WO | WO 2005056069 A1 | 6/2005 |
| WO | WO-2005097313 A1 | 10/2005 |
| WO | WO-2005113883 A1 | 12/2005 |
| WO | WO-2006042704 A2 | 4/2006 |
| WO | WO-2006069732 A1 | 7/2006 |
| WO | WO-2006082242 A2 | 8/2006 |

\* cited by examiner

WATER-ABSORBING POLYMERIC PARTICLES AND METHOD FOR THE PRODUCTION THEREOF

CROSS-REFERENCE TO RELATED APPLICATIONS

This is the U.S. national phase of International Application No. PCT/EP2008/059496, filed Jul. 21, 2008, which claims the benefit of European patent Application No. 07113326.8, filed Jul. 27, 2007.

The present invention concerns water-absorbing polymeric particles with high fluid transportation and absorption performance, processes for their production and also the use in hygiene articles and packaging materials.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, such as guar derivatives for example. Such polymers are used as products capable of absorbing aqueous solutions to manufacture diapers, tampons, sanitary napkins and other hygiene articles, but also as water retaining agents in gardening.

To improve their performance characteristics, such as for example Saline Flow Conductivity (SFC) in the diaper and Absorbency under Load (AUL), water-absorbing polymeric particles are generally postcrosslinked. This postcrosslinking can be carried out in the aqueous gel phase. But preferably ground and classified (base) polymeric particles are surface coated with a postcrosslinker, dried and thermally postcrosslinked. The two expressions surface-crosslinked and postcrosslinked are in the following equally used. Useful postcrosslinkers for this purpose are compounds, which comprise two or more groups capable of forming covalent bonds with the carboxylate groups of the hydrophilic polymer. Other useful postcrosslinkers are multivalent ions as described in U.S. Pat. No. 4,043,952.

U.S. Pat. No. 5,599,335 discloses that coarser particles achieve a higher Saline Flow Conductivity (SFC) here for the swollen layer of gel. It is further taught that Saline Flow Conductivity (SFC) can be increased by postcrosslinking, but only always at the expense of the Centrifuge Retention Capacity (CRC) and hence the absorptive capacity of the water-absorbing polymeric particles.

It is common knowledge among those skilled in the art that Saline Flow Conductivity (SFC) can be increased at the expense of Centrifuge Retention Capacity (CRC) by increasing the degree of internal crosslinking (more crosslinker in base polymer) as well as by stronger postcrosslinking (more postcrosslinker).

WO 04/069293 discloses water-absorbing polymeric particles coated with water-soluble salts of polyvalent cations. The polymeric particles possess improved Saline Flow Conductivity (SFC) and improved absorption properties. No teaching is given how to optimize the wicking ability (FHA=Fixed Height Absorption).

WO 04/069404 discloses salt resistant water-absorbing resins containing particles of a particle size of not less than 106 μm and less 850 μm in an amount of not less than 90% having similar values of Absorbency under Load (AUL) and Centrifuge Retention Capacity (CRC) and improved Saline Flow Conductivity. However, no teaching is given how the particle size distribution has to be optimized to yield high absorption capacity (CRC) and optimize saline flow conductivity (SFC) and wicking ability (FHA) likewise.

WO 04/069915 describes a process for producing water-absorbing polymeric particles which combine high Saline Flow Conductivity (SFC) with strong capillary forces, i.e., the ability to suck up aqueous fluids against the force of gravity. The capillary action of the polymeric particles is achieved through a specific surface finish. The absorption capacity under load (AUL 0.7 psi) is not very high, in addition the wicking ability (FHA) is depressed by the coatings applied.

U.S. Pat. No. 5,731,365 describes a process for coating water-absorbing polymeric particles by spray-coating with dispersions of a film-forming polymer, however the combination of Saline Flow Conductivity (SFC) and the wicking ability (FHA) is still unsufficient.

WO 2005/044900 describes a process for coating water-absorbing polymeric particles with a surface crosslinking agent, dispersions of a thermoplastic polymer and insoluble inorganic powders and heat-treatment of the thus obtained particles. The insoluble inorganic powder might be used in an amount in the range from 0.01 to 5 wt. %. The products exhibit improved saline flow conductivity, however no teaching is given how to optimize wicking ability (FHA).

WO 2006/069732 describes a process for coating water-absorbing polymeric particles with a surface crosslinking agent, a thermoplastic polymer and optionally a wax. The coating is applied in the range of 0.1 wt. % and less, and the coating is followed by a heat treatment. No disclosure is made how to optimize Saline Flow Conductivity (SFC) and wicking ability (FHA).

None of the prior art documents teaches a process to produce water-absorbing polymeric particles with high saline flow conductivity, high absorption capacity (CRC, AUL 0.7 psi) and high wicking ability (FHA).

WO 2005/097313 describes a process for the production of highly liquid permeable (high SFC) water-absorbing polymeric particles by extruding the hydrogel from a perforated structure having perforations diameters in the range of 0.3 to 6.4 mm to thereby pulverize the hydrogel, however the absorption capacity is very low and no teaching is given how to increase the absorption capacity to technically and commercially acceptable levels.

WO 2004/024816 describes a process for coating water-absorbing polymeric articles with a surface crosslinking agent and aluminum sulfate and a heat-treatment of the thus obtained particles and a subsequent treatment with polyvinylamine.

WO 2006/042704 describes a process for the production of highly liquid permeable (high SFC) water-absorbing polymeric particles with narrow particle size distribution, which also exhibit high wicking ability expressed by a transport value (TV). The liquid permeability and the wicking ability are optimized vs. absorption capacity by adjusting the degree of neutralization of the base polymer before surface-crosslinking. The surface treated particles may be treated with water-insoluble metal phosphate. As optional treatment are coatings with a film-forming polymer, polycationic polymer, and surfactant are mentioned without referring to certain composition or amounts.

Ultrathin articles of hygiene require finely divided water-absorbing polymeric particles without coarse particles, since coarse particles would be perceptible and are rejected by the consumer. But the smaller the particles, the smaller the Saline Flow Conductivity (SFC). On the other hand, small polymeric particles also create smaller pores when swelling which improve fluid transportation by wicking ability (FHA) within the gel layer.

This is an important factor in ultrathin hygiene articles, since these may comprise construction elements which consist of water-absorbing polymeric particles to an extent which is in the range from 50% to 100% by weight, so that the polymeric particles in use not only perform the storage function for the fluid but also ensure active fluid transportation (wicking ability=FHA) and passive fluid transportation (saline flow conductivity=SFC). The greater the proportion of cellulose pulp which is replaced by water-absorbing polymeric particles or synthetic fibers, the more liquid transport has to be handled by the water-absorbing polymeric particles in addition to their storage function. Hence, improved water-absorbing polymeric particles are exhibiting good liquid storage and good liquid transport properties.

The present invention therefore has for its object to provide water-absorbing polymeric particles having a high saline flow conductivity (SFC) combined with a high Centrifuge Retention Capacity (CRC), high Absorbency under Load (AUL) and a adjustable wicking ability (FHA), and a process for producing them.

The present invention further has for its object to provide a process for producing water-absorbing polymeric particles, which produces white polymeric particles, which are free of noticeable odors, especially when loaded with fluid.

The present invention further has for its object to provide a process for producing water-absorbing polymeric particles, which produces white polymeric particles, which will retain their white color even when exposed to hot and humid conditions for prolongued times.

We have found that this object is achieved by providing water-absorbing material obtainable by a process comprising the steps of bringing particles of a non surface-crosslinked water-absorbing polymer in contact with
a) at least one postcrosslinker,
b) 10-1000 ppm, based on the non surface-crosslinked water-absorbing polymer, of at least one Nitrogen-containing water-soluble polymer of which the Nitrogen can be protonated, and
c) at least one hydrophobic polymer
and heat-treating the particles thus obtained at a temperature in the range from 120° C. to 300° C.

The present invention further has for its objective a process for producing these water-absorbing materials.

Further embodiments of the present invention are discernible from the claims, the description and the examples. It will be appreciated that the hereinbefore identified and the hereinafter still to be more particularly described features of the subject matter of the present invention are utilizable not only in the particular combination indicated but also in other combinations without leaving the realm of the present invention.

Centrifuge Retention Capacity is determined by EDANA (European Disposables and Nonwovens Association) recommended test method No. 441.2-02 "Centrifuge retention capacity".

Absorbency under Load is determined by EDANA (European Disposables and Nonwovens Association) recommended test method No. 442.2-02 "Absorption under pressure".

Saline Flow Conductivity (SFC) and Fixed Height Absorption (FHA) are described in the test method section hereinbelow.

According to the invention particles of a non surface-crosslinked water-absorbing polymer are treated. Preferred non surface-crosslinked water-absorbing polymers comprise in polymerized form
i) at least one ethylenically unsaturated acid functional monomer,
ii) at least one crosslinker
iii) if appropriate one or more ethylenically and/or allylically unsaturated monomers copolymerizable with i) and
iv) if appropriate one or more water-soluble polymers onto which the monomers i), ii) and if appropriate iii) can be at least partially grafted.

Useful monomers i) include for example ethylenically unsaturated carboxylic acids, such as acrylic acid, methacrylic acid, maleic acid, fumaric acid, and itaconic acid, or derivatives thereof, such as acrylamide, methacrylamide, acrylic esters and methacrylic esters. Acrylic acid and methacrylic acid are particularly preferred monomers. Acrylic acid is most preferable.

The water-absorbing polymers are crosslinked, i.e., the addition polymerization is carried out in the presence of compounds having two or more polymerizable groups, which can be free-radically interpolymerized into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in German patent application 103 31 450.4, mixed acrylates which, as well as acrylate groups, comprise further ethylenically unsaturated groups, as described in German patent applications 103 31 456.3 and 103 55 401.7, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids with polyols, such as diacrylate or triacrylate, for example butanediol diacrylate, butanediol dimethacrylate, ethylene glycol diacrylate, ethylene glycol dimethacrylate and also trimethylolpropane triacrylate and ally compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention utilizes di(meth)acrylates of polyethylene glycols, the polyethylene glycol used having a molecular weight between 300 and 1000.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether 40-tuply ethoxylated glycerol and also of altogether 40-tuply ethoxylated trimethylolpropane.

Very particularly preferred for use as crosslinkers ii) are diacrylated, dimethacrylated, triacrylated or trimethacrylated multiply ethoxylated and/or propoxylated glycerols as described for example in prior German patent application DE 103 19 462.2. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 10 ppm) in the water-absorbing polymer and the aqueous extracts of water-absorbing polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols or polyacrylic acids, preferably polyvinyl alcohol and starch.

The preparation of a suitable base polymer and also further useful hydrophilic ethylenically unsaturated monomers i) are described in DE-A 199 41 423, EP-A 686 650, WO 01/45758 and WO 03/14300. Also suitable polymers can be prepared in a reverse suspension polymerization process or in a gas-phase spray- or droplet-polymerization.

The reaction is preferably carried out in a kneader as described for example in WO 01/38402, or on a belt reactor as described for example in EP-A-955 086.

Hence suitable polymers may be spherical shaped or irregular shaped, and the particles may be porous or dense phase. In order to obtain a high free swell rate porous particles are advantageous, moreover porous and irregular shaped particles are more advantageous. Porosity can be introduced for example by rapid drying, by addition of blowing agents in the polymerization or prior to the base polymer drying step, and by low solids polymerization.

The acid groups of the hydrogels obtained are preferably more than 60 mol %, more preferably more than 63 mol %, even more preferably more than 66 mol %, and most preferably in the range from 66.5 to 71 mol %, and preferably not more than 78 mol %, more preferably not more than 75 mol %, even more preferably not more than 72 mol % neutralized, for which the customary neutralizing agents can be used, for example ammonia, amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metal ions, but most preference is given to sodium hydroxide, sodium carbonate or sodium bicarbonate and also mixtures thereof. Typically, neutralization is achieved by admixing the neutralizing agent as an aqueous solution or else preferably as a solid material.

It is also possible to neutralize from 0.001 mol % to 10 mol % of the acidic groups with basic compounds of elements in group II or III of the periodic system of elements. For example basic compounds comprising Mg, Ca, and Al can be used. Such compounds include the respective carbonates, bicarbonates, oxides, hydroxides, aluminates, and salts of these elements with organic acids. Examples of such salts are the acetates, propionates, lactates, citrates, and tartrates.

Neutralization can be carried out after polymerization, at the hydrogel stage. But it is also possible to neutralize up to 40 mol %, preferably from 10 to 30 mol % and more preferably from 15 to 25 mol % of the acid groups before polymerization by adding a portion of the neutralizing agent to the monomer solution and to set the desired final degree of neutralization only after polymerization, at the hydrogel stage. The monomer solution may be neutralized by admixing the neutralizing agent, either to a predetermined degree of pre-neutralization with subsequent postneutralization to the final value after or during the polymerization reaction, or the monomer solution is directly adjusted to the final value by admixing the neutralizing agent before polymerization. The hydrogel can be mechanically comminuted, for example by means of a meat grinder, in which case the neutralizing agent can be sprayed, sprinkled or poured on and then carefully mixed in. To this end, the gel mass obtained can be repeatedly minced for homogenization.

A degree of neutralization which is too low may give rise to unwanted thermal crosslinking effects in the course of the subsequent drying and also during the subsequent postcrosslinking of the base polymer which are able to reduce the Centrifuge Retention Capacity (CRC) of the water-absorbing polymer substantially, to the point of inutility.

When the degree of neutralization is too high, however, postcrosslinking may be less efficient, which leads to a reduced Saline Flow Conductivity (SFC) on the part of the swollen hydrogel.

An optimum result is obtained when the degree of neutralization of the base polymer is adjusted such as to achieve efficient postcrosslinking and thus a high Saline Flow Conductivity (SFC) while at the same time neutralization is carried on sufficiently for the hydrogel being produced to be dryable in a customary belt dryer, or other drying apparatuses customary on an industrial scale, without loss of Centrifuge Retention Capacity (CRC).

The neutralized hydrogel is then dried with a belt, fluidized bed, tower, shaft or drum dryer until the residual moisture content is preferably below 10% by weight and especially below 5% by weight, the water content being determined by EDANA (European Disposables and Nonwovens Association) recommended test method No. 430.2-02 "Moisture content". The dried hydrogel is subsequently ground and sieved, useful grinding apparatus typically including roll mills, pin mills or swing mills, the sieves employed having mesh sizes necessary to produce the water-absorbing polymeric particles.

Although the particle sizes of the water-absorbing particles (base polymer) may vary from 150-850 µm, certain narrow particle size distributions are preferred.

In one preferred embodiment preferably less than 2% by weight, more preferably less than 1.5% by weight and most preferably less than 1% by weight of the water-particles have a particle size of above 600 µm.

Preferably not less than 90% by weight, more preferably not less than 95% by weight, even more preferably not less than 98% by weight and most preferably not less than 99% by weight of the water absorbing particles have a particle size in the range from 150 to 600 µm.

Preferably not less than 70% by weight, more preferably not less than 80% by weight, even more preferably not less than 85% by weight and most preferably not less than 90% by weight of the water absorbing particles have a particle size in the range from 300 to 600 µm.

In another preferred embodiment preferably less than 30% by weight, more preferably less than 20% by weight, and even more preferably less than 10% by weight and most preferably less than 5% by weight of the water absorbing particles have a particle size of above 600 µm and below 700 µm. Preferably not less than 90% by weight, more preferably not less than 95% by weight, even more preferably not less than 98% by weight and most preferably not less than 99% by weight of the water absorbing particles have a particle size in the range from 150 to 700 μm.

Preferably not less than 70% by weight, more preferably not less than 80% by weight, even more preferably not less than 85% by weight and most preferably not less than 90% by weight of the water absorbing particles have a particle size in the range from 300 to 700 μm.

According to the present invention the non surface-crosslinked water-absorbing polymer (in the following also referred as base polymer) is brought in contact with a post-crosslinker a), a Nitrogen-containing water-soluble polymer b), of which the Nitrogen can be protonated, and a hydrophobic polymer c).

Useful postcrosslinkers a) are compounds comprising two or more groups capable of forming covalent bonds with the carboxylate groups of the polymers. Useful compounds are for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, DE-C 35 23 617 and EP-A 450 922, or β-hydroxy-alkylamides as described in DE-A 102 04 938 and U.S. Pat. No. 6,239,230. It is also possible to use compounds of mixed functionality, such as glycidol, 3-ethyl-3-oxetanemethanol (trimethylolpropaneoxetane), as described in EP-A 1 199 327, aminoethanol, diethanolamine, triethanolamine or compounds which develop a further functionality after the first reaction, such as ethylene oxide, propylene oxide, isobutylene oxide, aziridine, azetidine or oxetane, and their respective equivalent derivatives.

Useful postcrosslinkers a) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by German patent application 103 34 584.1 bicyclic amide acetals, by EP-A 1 199 327 oxetanes and cyclic ureas and by WO 03/031482 morpholine-2,3-dione and its derivatives.

Postcrosslinking is typically carried out by spraying a solution of the postcrosslinker onto the hydrogel or the dry base-polymeric particles. Spraying is followed by thermal drying, and the postcrosslinking reaction can take place not only before but also during drying.

Preferred postcrosslinkers a) are amide acetals or carbamic esters of the general formula I

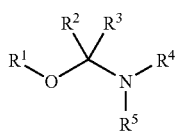

(I)

where
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl $R^5$ is hydrogen, $C_1$-$C_{12}$-alkyl, $C_2$-$C_{12}$-hydroxyalkyl, $C_2$-$C_{12}$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen common to $R^2$ and $R^3$, wherein $R^1$ and $R^4$ and/or $R^5$ and $R^6$ can be a bridged $C_2$-$C_6$-alkanediyl and wherein the abovementioned radicals $R^1$ to $R^6$ can still have in total one to two free valences and can be attached through these free valences to at least one suitable basic structure, or polyhydric alcohols, in which case the molecular weight of the polyhydric alcohol is preferably less than 100 g/mol, preferably less than 90 g/mol, more preferably less than 80 g/mol and most preferably less than 70 g/mol per hydroxyl group and the polyhydric alcohol has no vicinal, geminal, secondary or tertiary hydroxyl groups, and polyhydric alcohols are either diols of the general formula IIa

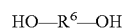

(IIa)

where $R^6$ is either an unbranched dialkyl radical of the formula $—(CH_2)_n—$, where n is an integer from 3 to 20 and preferably from 3 to 12, and both the hydroxyl groups are terminal, or an unbranched, branched or cyclic dialkyl radical or polyols of the general formula IIb

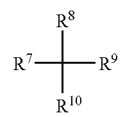

(IIb)

where $R^7$, $R^8$, $R^9$ and $R^{10}$ are independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and in total 2, 3 or 4 and preferably 2 or 3 hydroxyl groups are present, and not more than one of $R^7$, $R^8$, $R^9$ and $R^{10}$ is hydroxyl, or cyclic carbonates of the general formula III

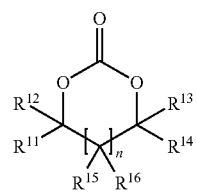

(III)

where $R^{11}$, $R^{12}$, $R^{13}$, $R^{14}$ and $R^{15}$ are independently hydrogen, methyl, ethyl, n-propyl, isopropyl, n-butyl, sec-butyl, isobutyl or hydroxyalkyl, $R^{16}$ is hydrogen, methyl, ethyl, n-propyl, isopropyl, n-butyl, sec-butyl, isobutyl, hydroxyalkyl or hydroxy and n is either 0 or 1.

or bisoxazolines of the general formula IV

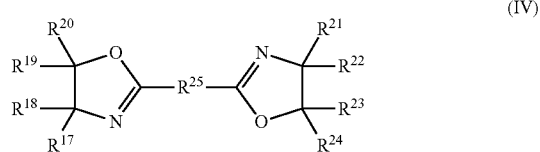

where $R^{17}$, $R^{18}$, $R^{19}$, $R^{20}$, $R^{21}$, $R^{22}$, $R^{23}$ and $R^{24}$ are independently hydrogen, methyl, ethyl, n-propyl, isopropyl, n-butyl, sec-butyl or isobutyl and $R^{25}$ is a single bond, a linear, branched or cyclic $C_1$-$C_{12}$-dialkyl radical or polyalkoxydiyl radical which is constructed of one to ten ethylene oxide and/or propylene oxide units, and is possessed by polyglycoldicarboxylic acids for example.

Preferred postcrosslinkers a) are selective reagents. Byproducts and secondary reactions, which lead to volatile and hence malodorous compounds are minimized. The water-absorbing polymers produced with preferred postcrosslinkers a) are therefore odor neutral even in the moistened state.

Epoxy compounds, by contrast, may at high temperatures in the presence of suitable catalysts undergo various rearrangement reactions, which lead to aldehydes or ketones for example. These can then undergo further secondary reactions, which eventually lead to the formation of malodorous impurities, which are undesirable in hygiene articles on account of their odor. Therefore, epoxy compounds are less suitable for postcrosslinking above a temperature of about 140 to 150° C. Amino- or imino-comprising postcrosslinkers a) will at similar temperatures undergo even more involved rearrangement reactions which tend to give rise to malodorous trace impurities and brownish product discolorations.

Polyhydric alcohols employed as postcrosslinkers a) require high postcrosslinking temperatures on account of their low reactivity. Alcohols comprising vincinal, geminal, secondary and tertiary hydroxyl groups, when employed as postcrosslinkers, give rise to byproducts which are undesirable in the hygiene sector because they lead to unpleasant odors and/or discolorations of the corresponding hygiene article during manufacture or use.

Preferred postcrosslinkers a) of the general formula I are 2-oxazolidones, such as 2-oxazolidone and N-(2-hydroxyethyl)-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxabicyclo[3.3.0]octane and 5-isopropyl-1-aza-4,6-dioxabicyclo[3.3.0] octane, bis-2-oxazolidones and poly-2-oxazolidones.

Particularly preferred postcrosslinkers a) of the general formula I are 2-oxazolidone, N-methyl-2-oxazolidone, N-(2-hydroxyethyl)-2-oxazolidone and N-hydroxypropyl-2-oxazolidone.

Preferred postcrosslinkers a) of the general formula IIa are 1,3-propanediol, 1,5-pentanediol, 1,6-hexanediol and 1,7-heptanediol. Further examples of postcrosslinkers of the formula IIa are 1,3-butanediol, 1,4-butanediole, 1,8-octanediol, 1,9-nonanediol and 1,10-decanediol.

The diols IIa are preferably soluble in water in that the diols of the general formula IIa dissolve in water at 23° C. to an extent of not less than 30% by weight, preferably not less than 40% by weight, more preferably not less than 50% by weight and most preferably not less than 60% by weight, examples being 1,3-propanediol and 1,7-heptanediol. Even more preference is given to such postcrosslinkers as are liquid at 25° C.

Preferred postcrosslinkers a) of the general formula IIb are 1,2,3-butanetriol, 1,2,4-butanetriol, glycerol, trimethylolpropane, trimethylolethane, pentaerythritol, ethoxylated glycerol, trimethylolethane or trimethylolpropane each having 1 to 3 ethylene oxide units per molecule, propoxylated glycerol, trimethylolethane or trimethylolpropane each having 1 to 3 propylene oxide units per molecule. Preference is further given to 2-tuply ethoxylated or propoxylated neopentylglycol. Particular preference is given to 2-tuply and 3-tuply ethoxylated glycerol and trimethylolpropane.

Preferred polyhydric alcohols IIa and IIb have a 23° C. viscosity of less than 3000 mPas, preferably less than 1500 mPas, more preferably less than 1000 mPas, even more preferably less than 500 mPas and most preferably less than 300 mPas.

Particularly preferred postcrosslinkers a) of the general formula III are ethylene carbonate and propylene carbonate.

A particularly preferred postcrosslinker a) of the general formula IV is 2,2'-bis(2-oxazoline).

The at least one postcrosslinker a) is typically used in an amount of not more than 0.30% by weight, preferably not more than 0.15% by weight and more preferably in the range from 0.001% to 0.095% by weight, all percentages being based on the base polymer, as an aqueous solution.

It is possible to use a single postcrosslinker a) from the above selection or any desired mixtures of various postcrosslinkers.

The aqueous postcrosslinking solution, as well as the at least one postcrosslinker a), can typically further comprise a cosolvent.

Cosolvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol or 1,4-butanediol, ketones, such as acetone, or carboxylic esters, such as ethyl acetate. The disadvantage with many of these cosolvents is that they have characteristic intrinsic odors.

The cosolvent itself is ideally not a postcrosslinker under the reaction conditions. However, in a borderline case and depending on the residence time and the temperature, the cosolvent may to some extent contribute to crosslinking. This will be the case in particular when the postcrosslinker a) is relatively inert and therefore is itself able to form its cosolvent, as with the use for example of cyclic carbonates of the general formula III, diols of the general formula IIa or polyols of the general formula IIb. Such postcrosslinkers a) can also be used as cosolvent when admixed with more reactive postcrosslinkers a), since the actual postcrosslinking reaction can then be carried out at lower temperatures and/or shorter residence times than in the absence of the more reactive crosslinker a). Since the cosolvent is used in relatively large amounts and will also remain to some extent in the product, it must neither be toxic, nor irritating, nor sensitizing.

In case such cosolvent is used alone and functions as crosslinker as well as a cosolvent, then its usage amount is less than 3% by weight, preferably less than 2% by weight, more preferably less than 1% by weight, and most preferably from 0.3 to 0.8% by weight based on the amount of polymeric particles to be coated. An example is the use of ethylenecarbonate dissolved in water.

The diols of the general formula IIa, the polyols of the general formula IIb and also the cyclic carbonates of the general formula III are also useful as cosolvents in the process of the present invention. They perform this function in the presence of a reactive postcrosslinker a) of the general formula I and/or IV and/or of a di- or triglycidyl crosslinker. However, preferred cosolvents in the process of the present invention are in particular the diols of the general formula IIa, especially when the hydroxyl groups are sterically hindered by neighboring groups from participating in a reaction. Such diols are in principle also useful as postcrosslinkers a), but for this require distinctly higher reaction temperatures or if appropriate higher use levels than sterically unhindered diols. Useful sterically hindered and hence reaction inert diols also include diols having tertiary hydroxyl groups.

Examples of such sterically hindered diols of the general formula IIa which are therefore particularly preferred for use as a cosolvent are 2,2-dimethyl-1,3-propanediol (neopentylglycol), 2-ethyl-1,3-hexanediol, 2-methyl-1,3-propanediol and 2,4-dimethylpentane-2,4-diol.

Particularly preferred cosolvents in the process of the present invention further include the polyols of the general formula IIb. Among these, the 2- to 3-tuply alkoxylated polyols are preferred in particular. But particularly useful cosolvents further include 3- to 15-tuply and most particularly 5- to 10-tuply ethoxylated polyols based on glycerol, trimethylolpropane, trimethylolethane or pentaerythritol. Seven-tuply ethoxylated trimethylolpropane and glycerole are particularly useful.

Useful cosolvents further include di(trimethylolpropane) and also 5-ethyl-1,3-dioxane-5-methanol.

Particularly preferred combinations of less reactive postcrosslinker a) as cosolvent and reactive postcrosslinker a) are combinations of preferred polyhydric alcohols, diols of the general formula IIa and polyols of the general formula IIb, with amide acetals or carbamic esters of the general formula I.

Very particularly preferred combinations are 2-oxazolidone/1,3-propanediol and N-(2-hydroxyethyl)-2-oxazolidone/1,3-propanediol.

In a particular preferred embodiment of the present invention a combination of 2-oxazolidone/glycerole or N-(2-hydroxyethyl)-2-oxazolidone/glycerole or a mixture of 2-oxazolidone and/or N-(2-hydroxyethyl)-2-oxazolidone with 1,3-propanediol and/or glycerole which is applied from an all aqeous solution or from a solvent mix of water and isopropanole is used.

Very particularly preferred combinations further include 2-oxazolidone or N-(2-hydroxyethyl)-2-oxazolidone as a reactive crosslinker combined with 1,5-pentanediol or 1,6-hexanediol or 2-methyl-1,3-propanediol or 2,2-dimethyl-1,3-propanediol, dissolved in water and/or isopropanol as non-reactive solvent.

In one embodiment of the present invention, the boiling point of the at least one postcrosslinker a) is preferably no higher than 160° C., more preferably no higher than 140° C. and most preferably no higher than 120° C., or is preferably no lower than 200° C., more preferably no lower than 220° C. and most preferably no lower than 250° C.

The boiling point of cosolvent is preferably no higher than 160° C., more preferably no higher than 140° C. and most preferably no higher than 120° C., or is preferably no lower than 200° C., more preferably no lower than 220° C. and most preferably no lower than 250° C.

Particularly useful cosolvents in the process of the present invention therefore also include those, which form a low boiling azeotrope with water or with a second cosolvent. The boiling point of this azeotrope is preferably no higher than 160° C., more preferably no higher than 140° C. and most preferably no higher than 120° C. Water vapor volatile cosolvents are likewise very useful, since they can be wholly or partly removed with the water evaporating in the course of drying.

The concentration of cosolvent in the aqueous postcrosslinker solution is frequently in the range from 15% to 50% by weight, preferably in the range from 15% to 40% by weight and more preferably in the range from 20% to 35% by weight, based on the postcrosslinker solution. In the case of cosolvents having a limited miscibility with water, it will be advantageous to adjust the aqueous postcrosslinker solution such that there is only one phase, if appropriate by lowering the concentration of cosolvent.

A preferred embodiment does not utilize any cosolvent. The at least one postcrosslinker a) is then only employed as a solution in water, with or without an added deagglomerating assistant.

The concentration of the at least one postcrosslinker a) in the aqueous postcrosslinker solution is for example in the range from 1% to 50% by weight, preferably in the range from 1.5% to 10% by weight and more preferably in the range from 2% to 5% by weight, based on the postcrosslinker solution.

The total amount of postcrosslinker solution based on the non surface-crosslinked water-absorbing polymer is usually in the range from 0.3% to 15% by weight and preferably in the range from 2% to 6% by weight.

Suitable Nitrogen-containing polymers, of which the nitrogen-functions can be protonated are for example polyvinylamine and partially hydrolysed polyvinylformamide or polyvinylacetamide, polyallylamine, and thermally stable derivatives of polyethyleneimine. The polymer can be linear, branched or dendritic. Polyvinylamine can be used in the form as obtained when its pre-cursor polyvinylformamide/-acetamide is fully hydrolysed which means that from 0 mol % to less than 10 mol % of the hydrolysable vinylformamide/-acetamide-groups stay unhydrolysed. Technically equivalent derivatives of the above polymers can also be used as long as these are thermally sufficiently stable against decomposition during the coating process.

In case the nitrogen-containing polymers are used as aqueous solutions it is preferable to apply them in their at least partially neutralized forms. Any organic acid or inorganic acid may be used for neutralization but preferably the partially neutralized polymer will remain fully dissolved. Useful acids for example but not limited to are hydrochloric acid, formic acid, acetic acid, propionic acid, and amidosulfonic acid.

The Nitrogen-containing water-soluble polymers of which the Nitrogen can be protonated may be used in mixture with polyvinylpyrrolidone, polyvinylimidazole and/or Polyvinylcaprolactame.

However, most preferred nitrogen-containing polymers in the present invention are partially hydrolysed pre-cursors of polyvinylamine for example partially hydrolysed polyvinylformamide with about 5-17 mol/kg nitrogen functions which can be protonated. They are disclosed in WO 2004/024816, and hereby expressly incorporated by reference. Mixtures of such polymers can be used. Preferred are partially hydrolysed polyvinylformamide or partially hydrolysed polyvinylacetamide in which from 20 mol % to 80 mol %, preferably 40 to 60 mol % of the hydrolysable vinylformamide/-acetamide-groups are hydrolysed and hereby converted to amino-groups which may be protonated.

The nitrogen-containing polymer is present in an amount up to 1000 ppm and preferably not more than 700 ppm, more preferably not more than 500 ppm, even more preferably not more than 300 ppm and most preferably not more than 250 ppm and preferable more than 10 ppm, more preferably more than 50 ppm, even more preferably more than 80 ppm, most preferably more than 100 ppm and most preferably in the range from 120 to 250 ppm, based on the non surface-crosslinked water-absorbing polymer. If the usage amount is too low then there is not a sufficient increase in SFC. If the usage amount is too high then the Absorption under load is depressed and falls below 21 g/g.

Suitable hydrophobic polymers may have film-forming properties, and very preferably they exhibit elastomeric physical properties. They are disclosed in U.S. Pat. No. 5,731, 365 and in EP 0703265, and also in WO 2006/082242 and WO 2006/097389, which are expressly incorporated in here by reference. Most preferred hydrophobic polymers are polyurethanes, poly(meth)acrylates, which optionally can be cross-linked by e.g. Zn, polyacrylates, and copolymers of styrene-(meth)acrylate, and copolymers of styrene and/or (meth)acrylate comprising acrylonitrile, copolymers of butadiene-styrene and/or acrylonitrile, (co)polymers of (crosslinkable) N-Vinylpyrrolidone and (co)polymers of vinylacetate. Most preferred hydrophobic polymers are polyurethanes. In case the hydrophobic polymer is film-forming it is preferred that the minimum film forming temperature is above −10° C., preferably above 20° C., more preferably above 50° C., and most preferably above 80° C.

The hydrophobic polymer is preferably applied as aqueous dispersion and optionally coalescing agents and/or anti-oxidants may be added.

The hydrophobic polymer is present in an amount up to 0.50 wt. % and preferably not more than 0.2 wt. %, more preferably not more than 0.15 wt. %, even more preferably not more than 0.1 wt. %, preferably not more than 0.05 mol % and most preferably not more than 0.03 wt. % and preferably more than 0.001 wt. %, more preferably more than 0.005 wt. %, even more preferably more than 0.008 wt. %, and most preferably in the range from 0.01 to 0.03 wt. %, based on the non surface-crosslinked water-absorbing polymer. In case that more than 0.5 wt. % is used the cost is high and the depression of FHA to very low values is prohibitive. In case no or too little of the hydrophobic polymer is used, the SFC is not sufficiently increased.

The present invention further provides a process for producing a water-absorbing material comprising the steps of bringing particles of a non surface-crosslinked water-absorbing polymer in contact with
a) a postcrosslinker,
b) 10-1000 ppm, based on the non surface-crosslinked water-absorbing polymer, of at least one Nitrogen-containing water-soluble polymer of which the Nitrogen can be protonated, and
c) at least one hydrophobic polymer
and heat-treating the particles thus obtained at a temperature in the range from 120° C. to 300° C.

According to a preferred embodiment the amount of Nitrogen-containing water-soluble polymer is in the range of 50 to 1000 ppm and the amount of the hydrophobic polymer is up to 0.2 wt. %, and preferably in the range from 0.02 to 0.15 wt. %, each based on the non surface-crosslinked water absorbing polymer.

The subsequent heat treatment takes place at ≥120° C., preferably at ≥150° C., more preferably ≥165° C., even more preferably ≥170° C., most preferably at a temperature in the range from 175° C. to 210° C., and usually not higher than 300° C. for a duration of between 5 minutes and 80 minutes, preferably between 30 minutes and 60 minutes.

The present invention further provides a process for producing water-absorbing polymers by polymerization of a monomer solution comprising
i) at least one ethylenically unsaturated acid functional monomer,
ii) at least one crosslinker,
iii) if appropriate one or more ethylenically and/or allylically unsaturated monomers copolymerizable with i),
iv) if appropriate one or more water-soluble polymers grafted wholly or partly with the monomers i), ii) and if appropriate iii),
the polymer obtained being dried, classified, and brought in contact with
a) a postcrosslinker,
b) 10-1000 ppm, based on the non surface-crosslinked water-absorbing polymer, of at least one Nitrogen-containing water-soluble polymer of which the Nitrogen can be protonated, and
c) at least one hydrophobic polymer
and heat-treating the particles thus obtained at a temperature in the range from 120° C. to 300° C.

According to a preferred process the heat-treating is stopped when the water-absorbing material has a Centrifuge Retention Capacity (CRC) of more than 25 g/g and an AUL 0.7 psi of more than 21 g/g and a SFC of not less than 80×10$^{-7}$ cm$^3$s/g, and exhibit the desired FHA.

The dried non-surface-crosslinked water-absorbing polymeric particles used in the process of the present invention typically have a residual moisture content in the range from 0% to 13% by weight and preferably in the range from 2% to 9% by weight after drying and before application of the postcrosslinking solution. Optionally, however, this moisture content can also be raised up to 75% by weight, for example by applying water in an upstream spraying mixer. The moisture content is determined by EDANA (European Disposables and Nonwovens Association) recommended test method No. 430.2-02 "Moisture content". Such an increase in the moisture content leads to a slight preswelling of the base polymer and improves the distribution of the postcrosslinker on the surface and also the penetration through the particles.

In a most preferred embodiment of the present invention the residual moisture content is in the range of 0% to 13% by weight and the temperature of the dried and sized base polymer is at least 40° C., preferably at least 50° C., more preferably at least 60° C., even more preferably at least 70° C., and most preferably between 80 and 110° C., and typically no more than 140° C. when the postcrosslinking solution a), and the solution comprising Nitrogen-containing water-soluble polymer b), and the hydrophobic polymer dispersion d) are sprayed on, and the coated warm polymer is subsequently transferred to the heat-treating step.

In a most preferred embodiment the postcrosslinker a) and the Nitrogen-containing water-soluble polymer b) and if appropriate above and/or below mentioned additional coating agents are sprayed as a postcrosslinker solution and the hydrophobic polymer d) and if appropriate above and/or below mentioned additional coating agents, is sprayed parallel as dispersion.

In the following all components which are sprayed in the postcrosslinking step, irrespective if they are sprayed in one mixture or in parallel mixtures, they are referred as postcrosslinker mixture.

Spray nozzles useful in the process of the present invention are not subject to any restriction. Such nozzles can be pressure fed with the liquid to be spray dispensed. The atomizing of the liquid to be spray dispensed can in this case be effected by decompressing the liquid in the nozzle bore after the liquid has reached a certain minimum velocity. Also useful are one-material nozzles, for example slot nozzles or swirl or whirl chambers (full cone nozzles) (available for example from Düsen-Schlick GmbH, Germany or from Spraying Systems Deutschland GmbH, Germany). Such nozzles are also described in EP-A-0 534 228 and EP-A-1 191 051.

After spraying, the polymeric powder is heat-treated. During this treatment the postcrosslinking reaction can take place. It is possible to have a phase with reduced temperature before or after the heat-treatment wherein the powder is dried.

The spraying with the postcrosslinker mixture is preferably carried out in mixers having moving mixing elements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers, Ruberg® mixers, Turbolizer® mixers and Schugi® mixers.

Drying can take place in the mixer itself, for example by heating the jacket or introducing a stream of warm air. It is similarly possible to use a downstream dryer, for example a tray dryer, a rotary tube oven or a heatable screw. But it is also possible for example to utilize an azeotropic distillation as a drying process.

Contact dryers are preferable, shovel dryers more preferable and disk dryers most preferable as apparatus in which thermal drying is carried out. Suitable dryers include for example Bepex® dryers and Nara® dryers. Fluidized bed dryers and tower dryers can be used as well, in particular when operated in continuous mode.

It is particularly preferable to apply postcrosslinker mixture in a high speed mixer, for example of the Schugi-Flexomix® or Turbolizer type, to the base polymer and the latter can then be thermally postcrosslinked in a reaction dryer, for example of the Nara-Paddle-Dryer type, or a disk dryer. The base polymer (non surface-crosslinked water-absorbing polymer) used can still have a temperature in the range from 10 to 140° C., preferably in the range from 40 to 110° C., more preferably from 50 to 100° C., even more preferably from 60 to 95° C., and most preferably from 70 to 85° C. from preceding operations, and the postcrosslinking mixture can have a temperature in the range from 0 to 150° C. More particularly, the postcrosslinking mixture can be heated to lower the viscosity. The preferred heat-treating temperature range is from 120 to 220° C., especially from 150 to 210° C. and most preferably from 160 to 195° C. The preferred residence time at this temperature in the reaction mixer or dryer is below 100 minutes, more preferably below 70 minutes and most preferably below 40 minutes.

The heat-treating dryer is flushed with air or preferably with an inert gas to remove vapors during the drying and postcrosslinking reaction. To augment the drying process, the dryer and the attached assemblies are ideally fully heated. Inert gases in the present invention are for example, but not limited to, nitrogen, argon, water vapor, carbon dioxide, noble gases, and are described in WO 2006/058682.

Cosolvents removed with the vapors may of course be condensed again outside the reaction dryer and if appropriate recycled.

In a preferred embodiment the heat-treating step is accomplished in the absence of oxygen by flushing the heat-treating dryer with inert gases and reducing the oxygen content to preferably less than 10 Vol. %, more preferably less than 1 Vol. %, even more preferably less than 0.01 Vol. %, and most preferably less than 0.001 Vol. %.

In a particular preferred embodiment the heat-treating step is accomplished in the absence of oxygen and with a non surface-crosslinked water absorbing polymer (base polymer) produced from monomers with low amounts of inhibitor as described in WO 2006/058682 which is expressly incorporated in here by reference.

In addition, additional coating agents may be used before, during or after heat-treating as follows:

Surfactants like for example sorbitan monoester, such as sorbitan mono-cocoate and sorbitan monolaurate, or ethoxylated variants thereof. Very useful surfactants further include the ethoxylated and alkoxylated derivatives of 2-propylheptanol, which are marketed by BASF Aktiengesellschaft of Germany under the brandnames of Lutensol® XL and Lutensol XP. Also for example Rewoderm S 1333 (CTFA: Disodium Monoricinoleamido MEA Sulfosuccinate 977 060-63-1) may be used.

Particularly preferred surfactants are non-ionic or amphoteric and contain at least one OH- or NH-group functionality per molecule that is capable of forming a covalent bond with a COOH-group. However, anionic or cationic surfactants can also be used as long as surface tension stays in the limits as described below.

The useful level of surfactant based on base polymer is for example in the range from 0% to 0.02% by weight, preferably in the range from 0% to 0.005% by weight, more preferably in the range from 0.0005% to 0.004% by weight, and most preferably in the range of 0.001 to 0.003% by weight. The surfactant is preferably dosed such that the surface tension of an aqueous extract of the swollen base polymer and/or of the swollen water-absorbing material is not less than 0.060 N/m, preferably not less than 0.062 N/m, and more preferably not less than 0.065 N/m, and most preferably not less than 0.069 N/m, and advantageously not more than 0.072 N/m, at 23° C.

The surfactant can be added separately or parallel to or as a mixture with the postcrosslinker. Preferably the surfactant is mixed with the postcrosslinker solution.

Optionally a dedusting agent like any of the above polyols can be used after the heat-treating step in order to bind dust to the water-absorbing polymeric particles. In such case it will be used in an amount of no more than 0.5 wt. %. Preferred dedusting agents are glycerole and 1.2-propandiol. Dedusting agents ideally do not have the ability to crosslink the polymer or are ideally applied under conditions when no crosslinking reaction takes place or only a small amount of the dedusting agent is consumed by a cross-linking reaction and the major part still is available in unreacted form on the surface of the hydrophilic particles to provide adhesion. Preferred dedusting agents are dendritic polymers, highly branched polymers, such as polyglycerines, polyethylene glycols, polypropylene glycols, random or block copolymers of ethylene oxide and propylene oxide. Useful dedusting agents for this purpose further include the polyethoxylates or polypropoxylates of polyhydroxy compounds, as of glycerol, sorbitol, trimethylolpropane, trimethylolethane and pentaerythritol. Examples thereof are n tuply ethoxylated trimethylolpropane or glycerol, n representing an integer between 1 and 100. Further examples are block copolymers, such as altogether n tuply ethoxylated and then multiply propoxylated trimethylolpropane or glycerol, n representing an integer between 1 and 40 and m representing an integer between 1 and 40. The order of the blocks can also be reversed. Suitable dustproofing agents are also simple polyols like 1.2-propandiole, glycerole, trimethylolpropane, and trimethylolethane.

Optionally one or more water-soluble metal salts may be sprayed as aqueous solution or as aqueous dispersion onto the water-absorbing polymeric particles before, during or after heat-treating. The water-soluble metal salt is mixed with the post-crosslinker solution or may be sprayed on separately in coincidental order, timewise overlapping order or in sequential order with the post-crosslinker solution. Preferably the water-soluble metal salt is mixed with the postcrosslinker solution. As used herein, the term "water-soluble" denotes a solubility of ≥1 g in 1000 ml of water at 25° C. Preferred water-soluble/-dispersible salts are for example—but not limited to—hydroxides, carbonates, hydrogencarbonates, sulfates, acetates, propionates, citrates, tartrates, and lactates of earth alkaline metals (Mg, Ca, Sr, Ba), Al and Zn. Most preferred are salts comprising Calcium and Strontium—for example Calciumhydroxide and Strontiumhydroxide. Preferred are water-soluble metal salts with a solubility of ≥10 g in 1000 ml of water at 25° C. Especially useful multivalent metal salts are listed in U.S. Pat. No. 4,043,952 which is expressly incorporated in here by reference. Examples of suitable metal salts but not limited to are sulfates, acetates, propionates, citrates, tartrates, and lactates of Aluminum, Calcium, Strontium, Zink, and Magnesium. Coating can be done for example in the amounts and as described in WO 2005/080479.

Optionally a solution of silica sol is applied as coating to the surface of the coated water absorbing polymeric particles to reduce stickiness. Very suitable are silica sols, which are sold under the trade name Levasil® by Hermann C Starck GmbH, Leverkusen. Such silica sols are sprayed on as aqueous solutions and are typically used in an amount of 0.01-1.0 wt. % calculated as silica based on the amount of water-absorbing polymeric particles to be coated. The silica sol can be added at any step in the process but is preferably coated as the outermost coating shell.

Optionally amorphous silica or metal oxides like MgO, ZnO, $TiO_2$, $Al_2O_3$, $ZrO_2$ in any form can be applied as coating to the surface of the coated water absorbing polymeric particles to reduce stickiness. Such agents are typically used in an amount of 0.01-1.0 wt. % calculated based on the amount of water-absorbing polymeric particles to be coated. Such agents can be added as powder blends, jetted in as powders, or sprayed on as aqueous dispersions. They can be added at any step in the process but are preferably coated as the outermost coating shell.

Optionally a wax is applied as coating to the surface of the coated water absorbing polymeric particles to reduce stickiness. Suitable waxes are described in U.S. Pat. No. 5,840,321 which is expressly incorporated in here by reference. Waxes are typically used in an amount of 0.01-1.0 wt. % calculated as wax based on the amount of water-absorbing polymeric particles to be coated. Such waxes can be added as powder blends, jetted in as powders, or sprayed on as aqueous dispersions. The wax can be added at any step in the process but is preferably coated as the outermost coating shell.

After the heat-treating step has been concluded, the dried water-absorbing material is cooled. To this end, the warm and dry polymer is preferably continuously transferred into a downstream cooler. This can be for example a disk cooler, a Nara paddle cooler or a screw cooler. Cooling is via the walls and if appropriate the stirring elements of the cooler, through which a suitable cooling medium such as for example warm or cold water flows. Water or aqueous solutions or aqueous dispersions of additives may preferably be sprayed on or blended-in in the cooler; this increases the efficiency of cooling (partial evaporation of water) and the residual moisture content in the finished product can be adjusted to a value in the range from 0% to 6% by weight, preferably in the range from 0.01% to 4% by weight and more preferably in the range from 0.1% to 3% by weight. The water content of the water-absorbing material according to the present invention is typically less than 20% by weight, preferably less than 6% by weight, more preferably less than 4% by weight and most preferably less than 3% by weight. The increased residual moisture content reduces the dust content of the product. If a dedusting agent is used, then it may be added in the cooler as aqueous solution. If optionally a surfactant or a water soluble multivalent metal salt is used it may be added in the cooler as aqueous solution or in a separate downstream mixing equipment like for example but not limited to a Lödige®- or a Ruberg®-Mixer.

Optionally, however, it is possible to use the cooler for cooling only and to carry out the addition of water and additives in a downstream separate mixer. Cooling stops the reaction by lowering the temperature to below the reaction temperature and the temperature needs altogether only to be lowered to such an extent that the product is easily packable into plastic bags or into silo trucks.

In particular when higher moisture contents are desired—i.e. up to 20% by weight—it is preferable to use a separate downstream mixer.

Optionally, however, all other known coatings to someone skilled in the art, such as water-insoluble polyvalent metal salts, such as calcium sulfate, water-soluble polyvalent metal salts, such as aluminum salts, calcium salts or magnesium salts, or water-soluble zirconium salts, or hydrophilic inorganic particles, such as clay minerals, can be additionally applied in the cooler or a subsequent separate coating step. This makes it possible to achieve additional effects, such as a reduced tendency to cake, improved processing properties or a further enhanced Saline Flow Conductivity (SFC). When the additives are used and sprayed in the form of dispersions, they are preferably used as aqueous dispersions, and it is optionally possible to apply a dustproofing agent to fix the additive on the surface of the water-absorbing polymer.

The process of the present invention is an effective way to obtain water-absorbing polymeric particles possessing superior fluid transportation properties and good absorption performance. The process also allows to optimize FHA and SFC for a given diaper design. The designer of a disposable diaper is hereby provided with a process to tailor the properties of the water-absorbing polymeric particles for the respective diaper design.

Preferably less than 5% by weight, more preferably less than 2% by weight and most preferably less than 1% by weight of the polymeric particles have a particle size of less than 150 μm or preferably less than 200 μm. The particle size is determined by EDANA (European Disposables and Nonwovens Association) recommended test method No. 420.2-02 "Particle size distribution".

Water absorbing material according to the present invention is characterized as follows:

Although the particle sizes of the water absorbing material may vary from 150-850 μm, certain narrow particle size distributions are preferred.

In one preferred embodiment preferably less than 2% by weight, more preferably less than 1.5% by weight and most preferably less than 1% by weight of the water absorbing material has a particle size of above 600 μm.

Preferably not less than 90% by weight, more preferably not less than 95% by weight, even more preferably not less than 98% by weight and most preferably not less than 99% by weight of the water absorbing material has a particle size in the range from 150 to 600 μm.

Preferably not less than 70% by weight, more preferably not less than 80% by weight, even more preferably not less than 85% by weight and most preferably not less than 90% by weight of the water absorbing material has a particle size in the range from 300 to 600 μm.

In another preferred embodiment preferably less than 30% by weight, more preferably less than 20% by weight, and even more preferably less than 10% by weight and most preferably less than 5% by weight of the water absorbing material has a particle size of above 600 μm and below 700 μm. Preferably not less than 90% by weight, more preferably not less than 95% by weight, even more preferably not less than 98% by weight and most preferably not less than 99% by weight of the water absorbing material has a particle size in the range from 150 to 700 μm.

Preferably not less than 70% by weight, more preferably not less than 80% by weight, even more preferably not less than 85% by weight and most preferably not less than 90% by weight of the water absorbing material has a particle size in the range from 300 to 700 μm.

The Centrifuge Retention Capacity (CRC) of the water absorbing material is usually not less than 25 g/g, preferably not less than 26 g/g, more preferably not less than 27 g/g, even more preferably not less than 28 g/g and most preferably in the range from 29 to 35 g/g and usually not above 50 g/g.

The absorbency under a load of 4.83 kPa (AUL 0.7 psi) of water absorbing material is usually not less than 21 g/g, and typically not less than 22 g/g, preferably not less than 22.5 g/g, more preferably not less than 23 g/g, even more preferably not less than 23.5 g/g, and most preferably between 24 and 28 g/g, and usually not above 45 g/g.

The Saline Flow Conductivity (SFC) of the water absorbing material is usually not less than $50 \times 10^{-7}$ cm$^3$s/g, preferably not less than $80 \times 10^{-7}$ cm$^3$s/g, more preferably not less than $100 \times 10^{-7}$ cm$^3$s/g, even more preferably not less than $120 \times 10^{-7}$ cm$^3$s/g and most preferably not less than $150 \times 10^{-7}$ cm$^3$s/g and usually not above $1500 \times 10^{-7}$ cm$^3$s/g.

The optimum SFC will depend on the respective design of the hygiene article in which the water absorbing material will be incorporated and therefore certain ranges of SFC are particularly preferred, while for these selected ranges the CRC should be maximized in each instance. Depending on the particular design of such hygiene articles it may be necessary to also maximize the FHA and the free swell rate (FSR). It is particularly observed that by application of the nitrogen-containing polymers or the hydrophobic polymer in small amounts for the coating of the surface of the water-absorbing polymeric particles the SFC can be increased, and depending on the usage level of the hydrophobic polymer additional SFC can be gained at the expense of FHA. In such way the process is capable to deliver water-absorbing polymeric particles with tailor made performance.

In one especially preferred embodiment of the present invention the SFC is in the range from 100 to $200 \times 10^{-7}$ cm$^3$s/g, most preferably in the range of 120 to $150 \times 10^{-7}$ cm$^3$s/g.

In another especially preferred embodiment of the present invention the SFC is in the range from 300 to $500 \times 10^{-7}$ cm$^3$s/g, most preferably in the range of 350 to $450 \times 10^{-7}$ cm$^3$s/g.

In yet another especially preferred embodiment of the present invention the SFC is in the range from 500 to $700 \times 10^{-7}$ cm$^3$s/g, most preferably in the range of 550 to $650 \times 10^{-7}$ cm$^3$s/g.

Water absorbing material according to the present invention exhibits a free swell rate (FSR) of usually not less than 0.05 g/g·s, typically not less than 0.10 g/g·s, preferably not less than 0.15 g/g·s, more preferably not less than 0.20 g/g·s, even more preferably between 0.25 and 0.50 g/g·s, and usually not more than 1.00 g/g·s.

The water absorbing material of the present invention is notable for a high wicking ability (FHA). Wicking ability can be determined using the wicking test "Fixed Height Absorption (FHA)" as described herein below. The process of the present invention allows maximizing CRC and SFC, and allows adjustment of the FHA to a desired value by adjusting the coating amounts of the nitrogen containing polymer, and the hydrophobic polymer while it is using cost efficient state-of-the-art coating equipment.

According to the invention the water absorbing material has a good Centrifuge Retention Capacity (CRC) which is not less than 25 g/g, preferably not less than 26 g/g, more preferably not less than 27 g/g, even more preferably not less than 28 g/g, and most preferably in the range from 29 to 35 g/g, the absorbency under a load of 4.83 kPa (AUL 0.7 psi) is usually not less than 21 g/g, and typically not less than 22 g/g, preferably not less than 22.5 g/g, more preferably not less than 23 g/g, even more preferably not less than 23.5 g/g, and most preferably from 24 to 28 g/g, and the Fixed Height Absorption Capacity (FHA) is not less than 5 g/g, preferably not less than 10 g/g, more preferably not less than 15 g/g, even more preferably not less than 20 g/g, and most preferably is at least 21, 22, 23, 24, 25, 26 g/g and is not more than 35 g/g. The amounts (wt. %, ppm) above are given in respect to the amount of dry water-absorbing polymeric particles before coating.

Centrifuge Retention Capacity (CRC), Saline Flow Conductivity (SFC), Absorption under load (AUL 0.7 psi) and Fixed Height Absorption (FHA) are optimized via the degree of neutralization of the base polymer (non surface-crosslinked water-absorbing polymer) and via the reaction conditions during heat-treating, and in particular via the coating formulation chosen within the limits above.

The Fixed Height Absorption (FHA) typically runs through a maximum during the progress of the heat-treating, and is strongly controlled by the particle size distribution of the non surface-crosslinked water-absorbing polymer as well as the hydrophilicity of its surface. If the non surface-crosslinked water-absorbing polymer is too fine then the FHA is high but SFC is low. If the non surface-crosslinked water-absorbing polymer is too coarse then the FHA is low but the SFC is high. Hence it is an objective of the present invention to control the amount of particles with less than 200 μm and more than 600 μm—within the limits given above—to a level which still allows obtaining the desired optimized finished product performance. Particles between 150-200 μm and 600-700 μm may be contained in the finished product but require diligent process control to not deteriorate the finished product performance.

Furthermore, the water absorbing material of the present invention is substantially free of compounds, which lead to unpleasant odors especially during use.

In one preferred embodiment the water-absorbing material of the present invention when comprising earth alkaline metal ions is very white, which is necessary especially in ultrathin diapers having a high fraction of water-absorbing material. Even minimal color variations are visible through the thin topsheet of ultrathin diapers, which is not accepted by consumers. In particular water absorbing material of the present invention also will maintain their white color to a great extent even if stored unprotected at elevated temperatures (60° C.) under very humid conditions (90% r.h.) for prolonged periods of time (20 days).

The present invention further provides hygiene articles comprising water-absorbing material according to the present invention, preferably ultrathin diapers comprising an absorbent layer consisting of 50% to 100% by weight, preferably 60% to 100% by weight, more preferably 70% to 100% by weight, even more preferably 80% to 100% by weight and most preferably 90% to 100% by weight of water-absorbing material according to the present invention, the closure surrounding the absorbent layer not included of course.

The water-absorbing material of the present invention is also very advantageous for producing diapers, laminates and composite structures as described for example in WO 2005/097025, US-A 2003/0181115, US-A 2004/0019342, and US-A 2003/0181115.

To determine the quality of heat-treating, the dried water-absorbing materials are tested using the test methods described.

Methods:

The measurements should be carried out, unless otherwise stated, at an ambient temperature of 23±2° C. and a relative humidity of 50±10%. The water-absorbing material is thoroughly mixed through before measurement.

Centrifuge Retention Capacity (CRC)

Centrifuge Retention Capacity is determined by EDANA (European Disposables and Nonwovens Association) recommended test method No. 441.2-02 "Centrifuge retention capacity", except that for each example the actual sample having the particle size distribution reported in the example is measured.

Absorbency Under Load (AUL)

Absorbency under Load is determined by EDANA (European Disposables and Nonwovens Association) recommended test method No. 442.2-02 "Absorption under pressure", except that for each example the actual sample having the particle size distribution reported in the example is measured.

Fixed Height Absorption (FHA)

The FHA is a method to determine the ability of a swollen gel layer to transport fluid by wicking. It is executed and evaluated as described on page 9 and 10 in EP 01 493 453 A1.

The following adjustments need to be made versus this description:

Laboratory conditions are 23±2° C. and relative humidity is no more than 50%.

Glass frit: 500 ml glass frit P40, as defined by ISO 4793, nominal pore size 16-40 μm, thickness 7 mm, e.g. Duran Schott pore size class 3. At 20° C.: a 30 cm diameter disk must be capable of a water flow of 50 ml/min for a pressure drop of 50 mbar.

Flexible plastic Tygon tube, for connecting the separatory funnel with the funnel with frit. Length must be sufficient to allow for 20 cm vertical movement of the funnel.

Use of high wet strength cellulose tissue, maximum basis weight 24.6 g/cm$^2$, size 80×80 mm, minimum wet tensile strength 0.32 N/cm (CO direction), and 0.8 N/cm (MD direction), e.g. supplied by Fripa Papierfabrik Albert Friedrich KG, D-63883 Miltenberg.

The tissue is clamped with a metal ring on the bottom side of the sample holder.

Calculation:

$$FHA = (m3 - m2) \div (m2 - m1)$$

weight of absorbed saline solution per 1 g of AGM, with $m1$ = weight of empty sample holder in g,
$m2$ = weight of sample holder with dry AGM in g,
$m3$ = weight of sample holder with wet AGM in g.

FHA is only determined in the context of the present invention with a hydrostatic column pressure corresponding to FHA at 20 cm.

Saline Flow Conductivity

The method to determine the permeability of a swollen hydrogel layer 718 is the "Saline Flow Conductivity" also known as "Gel Layer Permeability" and is described in several references, including, EP A 640 330, filed on Dec. 1, 1993, U.S. Ser. No. 11/349,696, filed on Feb. 3, 2004, U.S. Ser. No. 11/347,406, filed on Feb. 3, 2006, U.S. Ser. No. 06/682,483, filed on Sep. 30, 1982, and U.S. Pat. No. 4,469,710, filed on Oct. 14, 1982. The equipment used for this method is described below.

Permeability Measurement System

FIG. 1 shows permeability measurement system 400 set-up with the constant hydrostatic head reservoir 414, open-ended tube for air admittance 410, stoppered vent for refilling 412, laboratory jack 416, delivery tube 418, stopcock 420, ring stand support 422, receiving vessel 424, balance 426 and piston/cylinder assembly 428.

FIG. 2 shows the piston/cylinder assembly 428 comprising a metal weight 512, piston shaft 514, piston head 518, lid 516, and cylinder 520. The cylinder 520 is made of transparent polycarbonate (e.g., Lexan®) and has an inner diameter p of 6.00 cm (area=28.27 cm$^2$) with inner cylinder walls 550 which are smooth. The bottom 548 of the cylinder 520 is faced with a US. Standard 400 mesh stainless-steel screen cloth (not shown) that is bi-axially stretched to tautness prior to attachment to the bottom 548 of the cylinder 520. The piston shaft 514 is made of transparent polycarbonate (e.g., Lexan®) and has an overall length q of approximately 127 mm. A middle portion 526 of the piston shaft 514 has a diameter r of 21.15 mm. An upper portion 528 of the piston shaft 514 has a diameter s of 15.8 mm, forming a shoulder 524. A lower portion 546 of the piston shaft 514 has a diameter t of approximately ⅝ inch and is threaded to screw firmly into the center hole 618 (see FIG. 3) of the piston head 518. The piston head 518 is perforated, made of transparent polycarbonate (e.g., Lexan®), and is also screened with a stretched US. Standard 400 mesh stainless-steel screen cloth (not shown). The weight 512 is stainless steel, has a center bore 530, slides onto the upper portion 528 of piston shaft 514 and rests on the shoulder 524. The combined weight of the piston head 518, piston shaft 514 and weight 512 is 596 g (±6 g), which corresponds to 0.30 psi over the area of the cylinder 520. The combined weight may be adjusted by drilling a blind hole down a central axis 532 of the piston shaft 514 to remove material and/or provide a cavity to add weight. The cylinder lid 516 has a first lid opening 534 in its center for vertically aligning the piston shaft 514 and a second lid opening 536 near the edge 538 for introducing fluid from the constant hydrostatic head reservoir 414 into the cylinder 520.

A first linear index mark (not shown) is scribed radially along the upper surface 552 of the weight 512, the first linear index mark being transverse to the central axis 532 of the piston shaft 514. A corresponding second linear index mark (not shown) is scribed radially along the top surface 560 of the piston shaft 514, the second linear index mark being transverse to the central axis 532 of the piston shaft 514. A corresponding third linear index mark (not shown) is scribed along the middle portion 526 of the piston shaft 514, the third linear index mark being parallel with the central axis 532 of the piston shaft 514. A corresponding fourth linear index mark (not shown) is scribed radially along the upper surface 540 of the cylinder lid 516, the fourth linear index mark being transverse to the central axis 532 of the piston shaft 514. Further, a corresponding fifth linear index mark (not shown) is scribed along a lip 554 of the cylinder lid 516, the fifth linear index mark being parallel with the central axis 532 of the piston shaft 514. A corresponding sixth linear index mark (not shown) is scribed along the outer cylinder wall 542, the sixth linear index mark being parallel with the central axis 532 of the piston shaft 514. Alignment of the first, second, third, fourth, fifth, and sixth linear index marks allows for the weight 512, piston shaft 514, cylinder lid 516, and cylinder 520 to be re-positioned with the same orientation relative to one another for each measurement.

The cylinder 520 specification details are:
Outer diameter u of the Cylinder 520: 70.35 mm
Inner diameter p of the Cylinder 520: 60.0 mm
Height v of the Cylinder 520: 60.5 mm The cylinder lid 516 specification details are:
Outer diameter w of cylinder lid 516: 76.05 mm
Inner diameter x of cylinder lid 516: 70.5 mm
Thickness y of cylinder lid 516 including lip 554: 12.7 mm
Thickness z of cylinder lid 516 without lip: 6.35 mm
Diameter a of first lid opening 534: 22.25 mm
Diameter b of second lid opening 536: 12.7 mm
Distance between centers of first and second lid openings 534 and 536: 23.5 mm The weight 512 specification details are:
Outer diameter c: 50.0 mm
Diameter d of center bore 530: 16.0 mm
Height e: 39.0 mm The piston head 518 specification details are
Diameter f: 59.7 mm
Height g: 16.5 mm
Outer holes 614 (14 total) with a 9.65 mm diameter h, outer holes 614 equally spaced with centers being 47.8 mm from the center of center hole 618
Inner holes 616 (7 total) with a 9.65 mm diameter i, inner holes 616 equally spaced with centers being 26.7 mm from the center of center hole 618
Center hole 618 has a diameter j of ⅝ inches and is threaded to accept a lower portion 546 of piston shaft 514.

Prior to use, the stainless steel screens (not shown) of the piston head 518 and cylinder 520 should be inspected for clogging, holes or over-stretching and replaced when necessary. An SFC apparatus with damaged screen can deliver erroneous SFC results, and must not be used until the screen has been replaced.

A 5.00 cm mark 556 is scribed on the cylinder 520 at a height k of 5.00 cm (±0.05 cm) above the screen (not shown) attached to the bottom 548 of the cylinder 520. This marks the fluid level to be maintained during the analysis. Maintenance of correct and constant fluid level (hydrostatic pressure) is critical for measurement accuracy.

A constant hydrostatic head reservoir 414 is used to deliver salt solution 432 to the cylinder 520 and to maintain the level of salt solution 432 at a height k of 5.00 cm above the screen (not shown) attached to the bottom 548 of the cylinder 520. The bottom 434 of the air-intake tube 410 is positioned so as to maintain the salt solution 432 level in the cylinder 520 at the required 5.00 cm height k during the measurement, i.e., bottom 434 of the air tube 410 is in approximately same plane 438 as the 5.00 cm mark 556 on the cylinder 520 as it sits on the support screen (not shown) on the ring stand 440 above the receiving vessel 424. Proper height alignment of the air-intake tube 410 and the 5.00 cm mark 556 on the cylinder 520 is critical to the analysis. A suitable reservoir 414 consists of a jar 430 containing: a horizontally oriented L-shaped delivery tube 418 for fluid delivery, a vertically oriented open-ended tube 410 for admitting air at a fixed height within the constant hydrostatic head reservoir 414, and a stoppered vent 412 for re-filling the constant hydrostatic head reservoir 414. Tube 410 has an internal diameter of xx mm. The delivery tube 418, positioned near the bottom 442 of the constant hydrostatic head reservoir 414, contains a stopcock 420 for starting/stopping the delivery of salt solution 432. The outlet 444 of the delivery tube 418 is dimensioned to be inserted through the second lid opening 536 in the cylinder lid 516, with its end positioned below the surface of the salt solution 432 in the cylinder 520 (after the 5.00 cm height of the salt solution 432 is attained in the cylinder 520). The air-intake tube 410 is held in place with an o-ring collar (not shown). The constant hydrostatic head reservoir 414 can be positioned on a laboratory jack 416 in order to adjust its height relative to that of the cylinder 520. The components of the constant hydrostatic head reservoir 414 are sized so as to rapidly fill the cylinder 520 to the required height (i.e., hydrostatic head) and maintain this height for the duration of the measurement. The constant hydrostatic head reservoir 414 must be capable of delivering salt solution 432 at a flow rate of at least 3 g/sec for at least 10 minutes.

The piston/cylinder assembly 428 is positioned on a 16 mesh rigid stainless steel support screen (not shown) (or equivalent) which is supported on a ring stand 440 or suitable alternative rigid stand. This support screen (not shown) is sufficiently permeable so as to not impede salt solution 432 flow and rigid enough to support the stainless steel mesh cloth (not shown) preventing stretching. The support screen (not shown) should be flat and level to avoid tilting the piston/cylinder assembly 428 during the test. The salt solution 432 passing through the support screen (not shown) is collected in a receiving vessel 424, positioned below (but not supporting) the support screen (not shown). The receiving vessel 424 is positioned on the balance 426 which is accurate to at least 0.01 g. The digital output of the balance 426 is connected to a computerized data acquisition system (not shown).

Preparation of Reagents (not Illustrated)

Jayco Synthetic Urine (JSU) 712 (see FIG. 4) is used for a swelling phase (see SFC Procedure below) and 0.118 M Sodium Chloride (NaCl) Solution is used for a flow phase (see SFC Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4)_2HPO_4$) 0.15 g
Calcium Chloride ($CaCl_2$) 0.19 g—[or hydrated calcium chloride ($CaCl_2.2H_2O$) 0.25 g]
Magnesium chloride ($MgCl_2$) 0.23 g—[or hydrated magnesium chloride ($MgCl_2.6H_2O$) 0.50 g]

To make the preparation faster, each salt is completely dissolved before adding the next one. Jayco synthetic urine may be stored in a clean glass container for 2 weeks. The solution should not be used if it becomes cloudy. Shelf life in a clean plastic container is 10 days.

0.118 M Sodium Chloride (NaCl) Solution: 0.118 M Sodium Chloride is used as salt solution 432. Using a weighing paper or beaker 6.90 g (±0.01 g) of sodium chloride is weighed and quantitatively transferred into a 1 L volumetric flask; and the flask is filled to volume with distilled water. A stir bar is added and the solution is mixed on a stirring plate until all the solids are dissolved.

Test Preparation

Using a solid reference cylinder weight (not shown) (40 mm diameter; 140 mm height), a caliper gauge (not shown) (e.g., Mitotoyo Digimatic Height Gage) is set to read zero. This operation is conveniently performed on a smooth and level bench top 446. The piston/cylinder assembly 428 without superabsorbent is positioned under the caliper gauge (not shown) and a reading, L1, is recorded to the nearest 0.01 mm.

The constant hydrostatic head reservoir 414 is filled with salt solution 432. The bottom 434 of the air-intake tube 410 is positioned so as to maintain the top part (not shown) of the liquid meniscus (not shown) in the cylinder 520 at the 5.00 cm mark 556 during the measurement. Proper height alignment of the air-intake tube 410 at the 5.00 cm mark 556 on the cylinder 520 is critical to the analysis.

The receiving vessel 424 is placed on the balance 426 and the digital output of the balance 426 is connected to a computerized data acquisition system (not shown). The ring stand 440 with a 16 mesh rigid stainless steel support screen (not shown) is positioned above the receiving vessel 424. The 16 mesh screen (not shown) should be sufficiently rigid to support the piston/cylinder assembly 428 during the measurement. The support screen (not shown) must be flat and level.

SFC Procedure 0.9 g (±0.05 g) of superabsorbent is weighed onto a suitable weighing paper using an analytical balance. 0.9 g (±0.05 g) of superabsorbent is weighed onto a suitable weighing paper using an analytical balance. The moisture content of the superabsorbent is measured according to the Edana Moisture Content Test Method 430.1-99 ("Superabsorbent materials—Polyacrylate superabsorbent powders—MOISTURE CONTENT—WEIGHT LOSS UPON HEATING" (February 99)). If the moisture content of the polymer is greater than 5%, then the polymer weight should be corrected for moisture (i.e., the added polymer should be 0.9 g on a dry-weight basis).

The empty cylinder 520 is placed on a level benchtop 446 and the superabsorbent is quantitatively transferred into the cylinder 520. The superabsorbent particles are evenly dispersed on the screen (not shown) attached to the bottom 548 of the cylinder 520 by gently shaking, rotating, and/or tapping the cylinder 520. It is important to have an even distribution of particles on the screen (not shown) attached to the bottom 548 of the cylinder 520 to obtain the highest precision result. After the superabsorbent has been evenly distributed on the screen (not shown) attached to the bottom 548 of the cylinder 520 particles must not adhere to the inner cylinder walls 550. The piston shaft 514 is inserted through the first lid opening 534, with the lip 554 of the lid 516 facing towards the piston head 518. The piston head 518 is carefully inserted into the cylinder 520 to a depth of a few centimeters. The lid 516 is then placed onto the upper rim 544 of the cylinder 520 while taking care to keep the piston head 518 away from the superabsorbent. The lid 516 and piston shaft 526 are then carefully rotated so as to align the third, fourth, fifth, and sixth linear index marks are then aligned. The piston head 518 (via the piston shaft 514) is then gently lowered to rest on the dry superabsorbent. The weight 512 is positioned on the upper portion 528 of the piston shaft 514 so that it rests on the shoulder 524 such that the first and second linear index marks are aligned. Proper seating of the lid 516 prevents binding and assures an even distribution of the weight on the hydrogel layer 718.

Swelling Phase: An 8 cm diameter fritted disc (7 mm thick; e.g. Chemglass Inc. # CG 201-51, coarse porosity) 710 is saturated by adding excess JSU 712 to the fritted disc 710 until the fritted disc 710 is saturated. The saturated fritted disc 710 is placed in a wide flat-bottomed Petri dish 714 and JSU 712 is added until it reaches the top surface 716 of the fritted disc 710. The JSU height must not exceed the height of the fitted disc 710.

The screen (not shown) attached to the bottom 548 of the cylinder 520 is easily stretched. To prevent stretching, a sideways pressure is applied on the piston shaft 514, just above the lid 516, with the index finger while grasping the cylinder 520 of the piston/cylinder assembly 428. This "locks" the piston shaft 514 in place against the lid 516 so that the piston/cylinder assembly 428 can be lifted without undue force being exerted on the screen (not shown).

The entire piston/cylinder assembly 428 is lifted in this fashion and placed on the fritted disc 710 in the Petri dish 714. JSU 712 from the Petri dish 714 passes through the fritted disc 710 and is absorbed by the superabsorbent polymer (not shown) to form a hydrogel layer 718. The JSU 712 available in the Petri dish 714 should be enough for all the swelling phase. If needed, more JSU 712 may be added to the Petri dish 714 during the hydration period to keep the JSU 712 level at the top surface 716 of the fritted disc 710. After a period of 60 minutes, the piston/cylinder assembly 428 is removed from the fritted disc 710, taking care to lock the piston shaft 514 against the lid 516 as described above and ensure the hydrogel layer 718 does not lose JSU 712 or take in air during this procedure. The piston/cylinder assembly 428 is placed under the caliper gauge (not shown) and a reading. L2, is recorded to the nearest 0.01 mm. If the reading changes with time, only the initial value is recorded. The thickness of the hydrogel layer 718, L0 is determined from L2–L1 to the nearest 0.1 mm.

The entire piston/cylinder assembly 428 is lifted in this the fashion described above and placed on the support screen (not shown) attached to the ring stand 440. Care should be taken so that the hydrogel layer 718 does not lose JSU 712 or take in air during this procedure. The JSU 712 available in the Petri dish 714 should be enough for all the swelling phase. If needed, more JSU 712 may be added to the Petri dish 714 during the hydration period to keep the JSU 712 level at the 5.00 cm mark 556. After a period of 60 minutes, the piston/cylinder assembly 428 is removed, taking care to lock the piston shaft 514 against the lid 516 as described above. The piston/cylinder assembly 428 is placed under the caliper gauge (not shown) and the caliper (not shown) is measured as L2 to the nearest 0.01 mm. The thickness of the hydrogel layer 718, L0 is determined from L2–L1 to the nearest 0.1 mm. If the reading changes with time, only the initial value is recorded.

The piston/cylinder assembly 428 is transferred to the support screen (not shown) attached to the ring support stand 440 taking care to lock the piston shaft 514 in place against the lid 516. The constant hydrostatic head reservoir 414 is positioned such that the delivery tube 418 is placed through the second lid opening 536. The measurement is initiated in the following sequence:

a) The stopcock 420 of the constant hydrostatic head reservoir 410 is opened to permit the salt solution 432 to reach the 5.00 cm mark 556 on the cylinder 520. This salt solution 432 level should be obtained within 10 seconds of opening the stopcock 420.

b) Once 5.00 cm of salt solution 432 is attained, the data collection program is initiated.

With the aid of a computer (not shown) attached to the balance 426, the quantity of salt solution 432 passing through the hydrogel layer 718 is recorded at intervals of 20 seconds for a time period of 10 minutes. At the end of 10 minutes, the stopcock 420 on the constant hydrostatic head reservoir 410 is closed. The piston/cylinder assembly 428 is removed immediately, placed under the caliper gauge (not shown) and a reading. L3, is recorded to the nearest 0.01 mm. The final thickness of the hydrogel layer 718, Lf is determined from L3–L1 to the nearest 0.1 mm, as described above. The percent change in thickness of the hydrogel layer 718 is determined from (Lf/L0)×100. Generally the change in thickness of the hydrogel layer 718 is within about ±10%.

The data from 60 seconds to the end of the experiment are used in the SFC calculation. The data collected prior to 60 seconds are not included in the calculation. The flow rate Fs (in g/s) is the slope of a linear least-squares fit to a graph of the weight of salt solution 432 collected (in grams) as a function of time (in seconds) from 60 seconds to 600 seconds.

In a separate measurement, the flow rate through the permeability measurement system 400 (Fa) is measured as described above, except that no hydrogel layer 718 is present. If Fa is much greater than the flow rate through the permeability measurement system 400 when the hydrogel layer 718 is present. Fs, then no correction for the flow resistance of the permeability measurement system 400 (including the piston/cylinder assembly 428) is necessary. In this limit, Fg=Fs, where Fg is the contribution of the hydrogel layer 718 to the flow rate of the permeability measurement system 400. However if this requirement is not satisfied, then the following correction is used to calculate the value of Fg from the values of Fs and Fa:

$$Fg = (Fa \times Fs)/(Fa - Fs)$$

The Saline Flow Conductivity (K) of the hydrogel layer 718 is calculated using the following equation:

$$K = [Fg(t=0) \times L0]/[\rho \times A \times \Delta P],$$

where Fg is the flow rate in g/sec determined from regression analysis of the flow rate results and any correction due to permeability measurement system 400 flow resistance. L0 is the initial thickness of the hydrogel layer 718 in cm, $\rho$ is the density of the salt solution 432 in gm/cm$^3$. A (from the equation above) is the area of the hydrogel layer 718 in cm$^2$, $\Delta P$ is the hydrostatic pressure in dyne/cm$^2$, and the saline flow conductivity, K, is in units of cm$^3$ sec/gm. The average of three determinations should be reported.

For hydrogel layers 718 where the flow rate is substantially constant, a permeability coefficient ($\kappa$) can be calculated from the saline flow conductivity using the following equation:

$$\kappa = K\eta$$

where $\eta$ is the viscosity of the salt solution 432 in poise and the permeability coefficient, $\kappa$, is in units of cm$^2$.

In general, flow rate need not be constant. The time-dependent flow rate through the system, Fs (t) is determined, in units of g/sec, by dividing the incremental weight of salt solution 432 passing through the permeability measurement system 400 (in grams) by incremental time (in seconds). Only data collected for times between 60 seconds and 10 minutes is used for flow rate calculations. Flow rate results between 60 seconds and 10 minutes are used to calculate a value for Fs (t=0), the initial flow rate through the hydrogel layer 718. Fs (t=0) is calculated by extrapolating the results of a least-squares fit of Fs (t) versus time to t=0.

FIGURES

16 h Extractables

Figure 1:
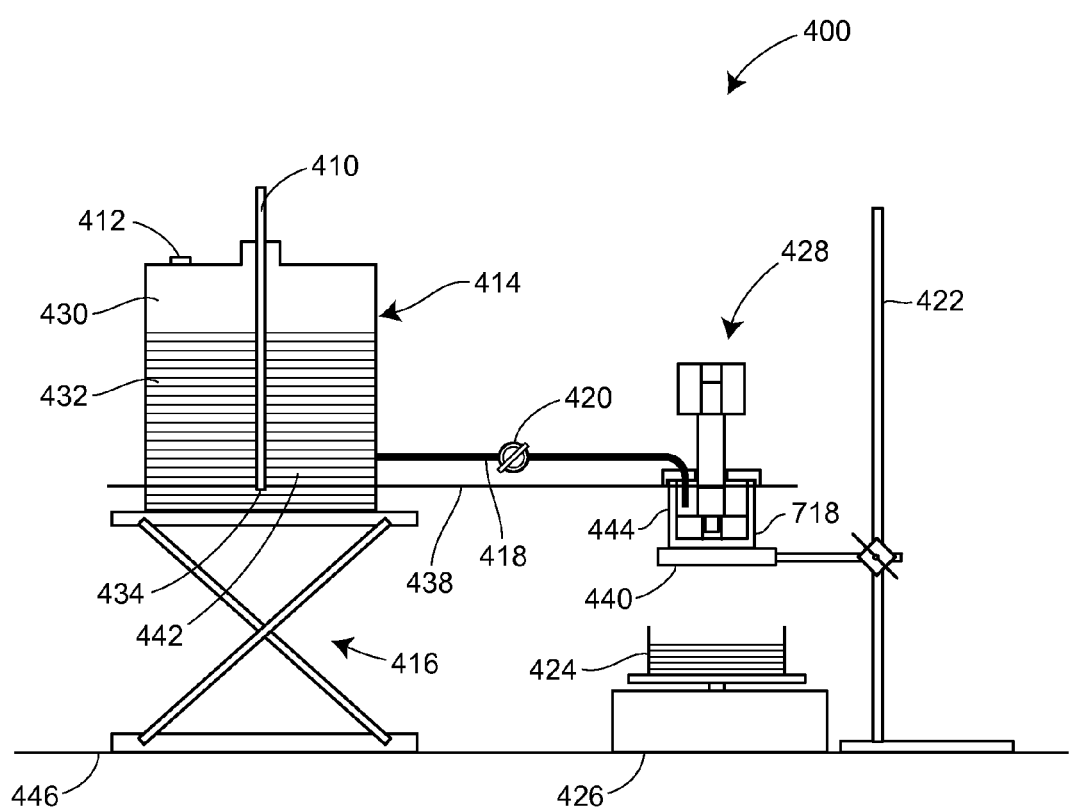
FIG. 1 is a partial cross-sectional side view of a suitable permeability measurement system for conducting the Saline Flow Conductivity Test.
Figure 2:
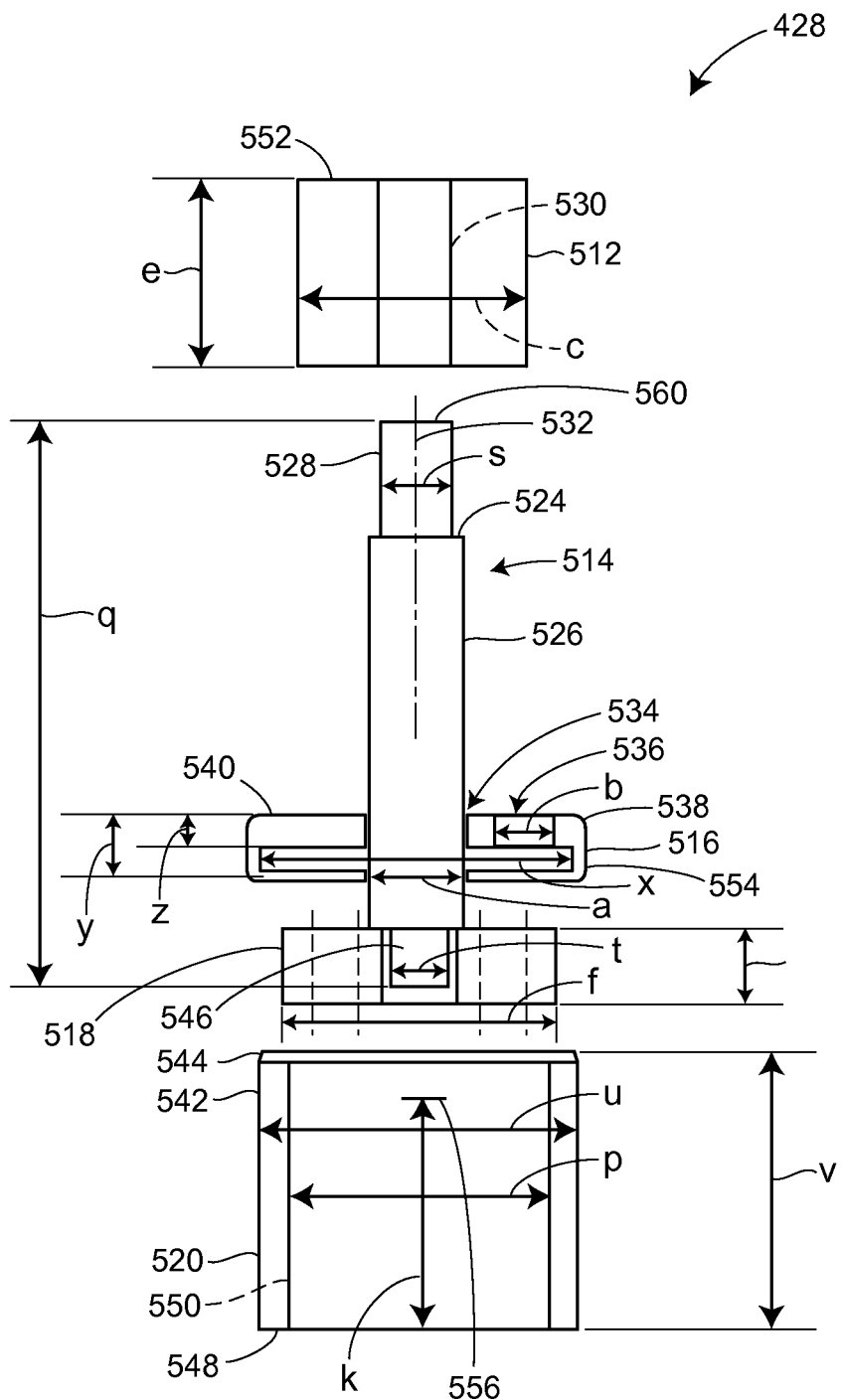
FIG. 2 is a cross-sectional side view of a piston/cylinder assembly for use in conducting the Saline Flow Conductivity Test.
Figure 3:
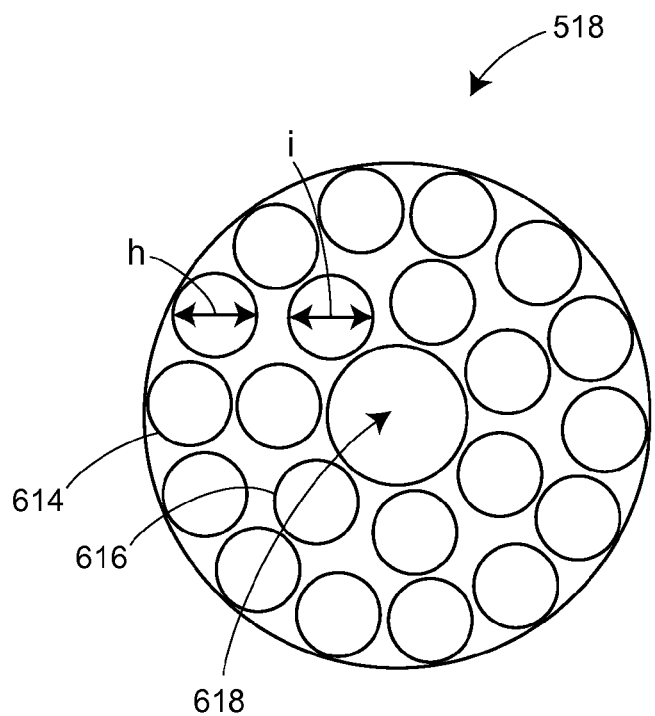
FIG. 3 is a top view of a piston head suitable for use in the piston/cylinder assembly shown in FIG. 2.
Figure 4:
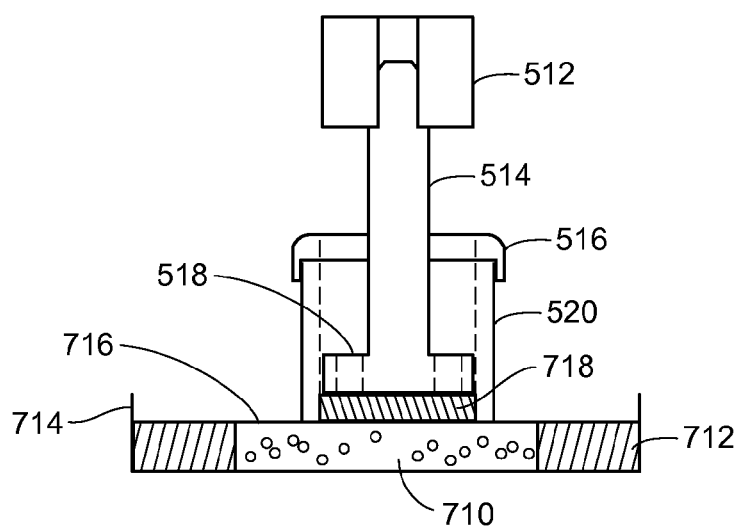
FIG. 4 is a cross-sectional side view of the piston/cylinder assembly of FIG. 2 placed on a fritted disc for the swelling phase.

The level of extractable constituents in the water-absorbing polymeric particles is determined by the EDANA (European Disposables and Nonwovens Association) recommended test method No. 470.2-02 "Determination of extractable polymer content by potentiometric titration".

pH Value

The pH of the water-absorbing material is determined by the EDANA (European Disposables and Nonwovens Association) recommended test method No. 400.2-02 "Determination of pH".

Free Swell Rate (FSR)

1.00 g (=W1) of the dry water-absorbing material is weighed into a 25 ml glass beaker and is uniformly distributed on the base of the glass beaker. 20 ml of a 0.9% by weight sodium chloride solution are then dispensed into a second glass beaker, the contents of this beaker are rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR[g/gs] = W2/(W1 \times t)$$

When the moisture content of the hydrogel-forming polymer is more than 3% by weight, however, the weight W1 must be corrected for this moisture content.

Surface Tension of Aqueous Extract 0.50 g of the water-absorbing material is weighed into a small glass beaker and admixed with 40 ml of 0.9% by weight salt solution. The contents of the beaker are magnetically stirred at 500 rpm for 3 minutes and then allowed to settle for 2 minutes. Finally, the surface tension of the supernatant aqueous phase is measured with a K10-ST digital tensiometer or a comparable apparatus having a platinum plate (from Kruess). The measurement is carried out at a temperature of 23° C.

Moisture Content of Hydrogel

The water content of the water-absorbing material is determined by the EDANA (European Disposables and Nonwovens Association) recommended test method No. 430.2-02 "Moisture content".

Odor Test

To assess the odor of the swollen water-absorbing material, 2.0 g of dry polymeric particles are weighed into a 50 ml glass beaker. 20 g of 0.9% by weight sodium chloride solution at 23° C. are then added. The glass beaker holding the swelling water-absorbing material is covered with Parafilm and left to stand for 3 minutes. Thereafter, the film is removed and the odor can be assessed. Each sample is examined by at least 3 test persons, a separate sample being prepared for each person.

CIE Color Number (L a b)

Color measurement was carried out in accordance with the CIELAB procedure (Hunterlab, volume 8, 1996, issue 7, pages 1 to 4). In the CIELAB system, the colors are described via the coordinates L*, a* and b* of a three-dimensional system. L* indicates lightness, with L*=0 denoting black and L*=100 denoting white. The a* and b* values indicate the position of the color on the color axes red/green and yellow/blue respectively, where +a* represents red, −a* represents green, +b* represents yellow and −b* represents blue.

The color measurement complies with the three-range method of German standard specification DIN 5033-6.

The Hunter 60 value is a measure of the whiteness of surfaces and is defined as L*-3b*, i.e., the lower the value, the darker and the yellower the color is.

A Hunterlab LS 5100 colorimeter was used.

The EDANA test methods are obtainable for example at European Disposables and Nonwovens Association, Avenue Eugène Plasky 157, B-1030 Brussels, Belgium.

EXAMPLES

Example 1

Preparation of Base Polymer

A Lödige VT 5R-MK plowshare kneader with 5 l capacity was charged with 206.5 g of deionized water, 271.6 g of acrylic acid, 2115.6 g of 37.3% by weight sodium acrylate solution (100 mol % neutralized) and also 3.5 g of a threefold ethoxylated glycerol triacrylate crosslinker. This initial charge was inertized by bubbling nitrogen through it for 20 minutes. This was followed by the addition of dilute aqueous solutions of 2.453 g of sodium persulfate (dissolved in 13.9 g of water), 0.053 g of ascorbic acid (dissolved in 10.46 g of water) and also 0.146 g of 30% by weight hydrogen peroxide (dissolved in 1.31 g of water) to initiate the polymerization at about 20° C. After initiation, the temperature of the heating jacket was controlled to follow exactly the reaction temperature inside the reactor. The crumbly gel ultimately obtained was then dried in a circulating air drying cabinet at 160° C. for about 3 hours.

The dried base polymer was ground and classified to 200-600 µm by sieving off over- and undersize particles.

The properties (averages) of the polymer were as follows:
Particle Size distribution (average):
<200 µm: 1.8% by weight
200-500 µm: 55.5% by weight
500-600 µm: 37.1% by weight
>600 µm: 5.5% by weight
CRC=35.6 g/g
AUL 0.3 psi=17.9 g/g
16 h extractables=12.7% by weight
pH=5.9

Example 2

Preparation of the Coating Solution (I) was as Follows 14.40 g Water,
11.47 g Isopropanol,
0.84 g 1,3-Propandiol,
0.85 g N-(2-Hydroxyethyl)-2-oxazolidinon,
0.036 g Sorbitanmonolaurat (ALDRICH) and
11.43 g of a 10.5% by weight aqueous solution of Poly-Vinylformamid/Vinylamine (mol ratio 1:1) (Luredur® PR 8097 of BASF AG, Germany)

The two components were charged in a beaker and stirred for few minutes by standard lab stirring equipment until a homogeneous solution was obtained.

Preparation of the hydrophobic coating dispersion (II) was as following:

3.16 g of a 38% by weight aqueous anionic, aliphatic Polyurethane dispersion of BASF AG, Germany, based on Polyetherols, pH ~8 (Astacin® Finish PUMN TF)
6.97 g Water The components were charged in a beaker and stirred for few minutes by standard lab stirring equipment until a homogeneous dispersion was obtained.

A Lödige plowshare mixer of 5 l capacity was charged at room temperature with 1200 g of base polymer according to example 1. At a revolution of 200 rpm 38.12 g of the coating solution (I) and 10.13 g of the coating dispersion (II) were sprayed independently but parallel onto the polymer particles within about 10 minutes, each via a 2-stuff nozzle while using Nitrogen of 1 bar pressure as atomizing gas and using a hose pump for feeding the coating suspension.

Directly after coating was finished the coated polymer particles were transferred into a second, already preheated Lödige plowshare mixer of 5 l in capacity (245° C. thermostat temperature) and heated up to 190° C. product temperature) for 60 minutes under Nitrogen inertization. With increasing product temperature, coming closer to target temperature the thermostat set-temperature was reduced to 215° C. and kept unchanged until end of the run. Starting 20 minutes after charging the preheated mixer it were taken samples frequently all 10 minutes for characterizing the polymer performance in dependency of residence time. To eliminate possible formed agglomerates the surface cross-linked polymer particles were sieved after finished heat treatment and before characterizing over a 600 µm screen.

Results are listed in table 1:

TABLE 1

Performance parameters after a residence time of 30 and 40 minutes

| | Example | |
|---|---|---|
| Residence time [min] | 30 | 40 |
| Product Temperature [° C.] | 190 | 190 |
| CRC [g/g] | 28.4 | 27.5 |
| AUL 0.7 psi [g/g] | 21.3 | 21.2 |
| SFC [$10^{-7}$ cm$^3$*s/g] | 318 | 425 |
| FHA [g/g] | 7.4 | 5.5 |

Examples 3-6

1200 g base polymer according to example 1 was surface coated fully analogous to example 2 with the difference, that the amount of the components of the coating solution (I) and coating dispersion (II) have been varied, especially of the applied hydrophilic and hydrophobic polymers (based on base polymer).

The preparation of the coating solution (I) as well as of the coating dispersion (II) was as described in example 2.

|  | Example 3 | Example 4 | Example 5 | Example 6 |
|---|---|---|---|---|
| Coating solution (I): | | | | |
| Water: | 22.11 g | 23.65 g | 23.18 g | 22.70 g |
| Isopropanol: | 12.37 g | 12.55 g | 12.55 g | 12.55 g |
| 1,3-Propandiol: | 0.84 g | 0.84 g | 0.84 g | 0.84 g |
| N-(2-Hydroxyethyl)-2-oxazolidinon: | 0.85 g | 0.85 g | 0.85 g | 0.85 g |
| Sorbitanmonolaurat (ALDRICH): | 0.036 g | 0.036 g | 0.36 g | 0.036 g |
| Luredur ® PR 8097 (10.5% solid content): | 2.86 g | 1.14 g | 1.14 g | 1.14 g |
| Coating dispersion (II): | | | | |
| Water: | 6.97 g | 6.97 g | 8.42 g | 9.68 g |
| Astacin ® Finish PUMN TF (38% solid content): | 3.16 g | 3.16 g | 1.58 g | 0.32 g |

Results are listed in table 2:

TABLE 2

Performance parameters after a residence time of 25, 30 and 50 minutes

| | Examples | | | | | | | | | |
|---|---|---|---|---|---|---|---|---|---|---|
| | 3 | | | 4 | | | 5 | | 6a | |
| Residence time [min] | 25 | 30 | 50 | 25 | 30 | 50 | 30 | 50 | 30 | 50 |
| Product Temperature [° C.] | 190 | 190 | 190 | 190 | 190 | 190 | 190 | 190 | 190 | 190 |
| CRC [g/g] | 30.4 | 29.0 | 26.8 | 30.4 | 29.3 | 27.2 | 29.2 | 25.8 | 28.8 | 25.4 |
| AUL 0.7 psi [g/g] | 22.6 | 22.6 | 21.3 | 22.8 | 22.7 | 21.6 | 24.3 | 22.6 | 23.1 | 22.0 |
| SFC [$10^{-7}$cm$^3$*s/g] | 128 | 225 | 478 | 125 | 331 | 462 | 140 | 386 | 133 | 392 |
| FHA [g/g] | 9.3 | 8.5 | 5.5 | 14 | 11 | 7 | 20 | 12 | 24 | 15 |

Examples 7-9

1200 g base polymer according to example 1 was surface coated fully analogous to example 2 with the difference that the amount of the components of the coating solution (I) and coating dispersion (II) varied, especially the percentage (weight % based on base polymer) of the hydrophilic and hydrophobic polymer.

The preparation of the coating solution (I) as well as of the coating dispersion (II) was as described in example 2.

|  | Example 7 | Example 8 | Example 9 |
|---|---|---|---|
| Coating solution (I): | | | |
| Water: | 16.11 g | 22.11 g | 22.11 |
| isopropanol: | 12.55 g | 12.55 g | 12.55 |
| 1,3-Propandiol: | 0.84 g | 0.84 g | 0.84 |
| N-(2-Hydroxyethyl)-2-oxazolidinon: | 0.85 g | 0.85 g | 0.85 g |
| Sorbitanmonolaurat (ALDRICH): | 0.036 g | 0.036 g | 0.36 g |
| Luredur ® PR 8097 (10.5% solid content): | 1.14 g | 1.14 g | 1.14 g |
| Aluminiumlactat (RIEDEL DE HAEN): | 6.00 g | none | none |
| Coating dispersion (II): | | | |
| Water: | 7.13 g | 3.29 g | 7.52 g |
| Poligen ® MA (40% solid content) [1]: | 3.00 g | none | none |
| Corial ® Ultrasoft NT (35% solid content) [2]: | none | 6.84 g | none |
| Mowilith ® DM 799 (46% solid content) [3]: | none | none | 2.61 |

[1] Aqueous anionic (Meth)arylic-copolymer dispersion of BASF AG, Germany/solid content ~40%
[2] Aqueous anionic Polyacrylate dispersion of BASF AG, Germany/pH ~8/solid content ~40%
[3] Acrylester copolymer dispersion of Celanes GmbH, Germany/solid content ~46%

Results are listed in the following table 3:

TABLE 3

Performance parameters after a residence time of 30 and 40 minutes

| | Examples | | |
|---|---|---|---|
| | 7 | 8 | 9 |
| Residence time [min] | 30 | 40 | 40 |
| Product Temperature [° C.] | 185 | 190 | 190 |
| CRC [g/g] | 29 | 28.1 | 28.7 |
| AUL 0.7 psi [g/g] | 24.1 | 23.6 | 24.1 |
| SFC [$10^{-7}$ cm$^3$*s/g] | 126 | 136 | 140 |
| FHA [g/g] | 22 | 16 | 23 |
| FSR [g/g/s] | 0.23 | 0.2 | 0.21 |

We claim:

1. A water absorbing material prepared by a process comprising bringing particles of a non surface-crosslinked water-absorbing polymer in contact with
   a) at least one postcrosslinker,
   b) 10-1000 ppm, based on the non surface-crosslinked water-absorbing polymer, of at least one nitrogen atom-containing water-soluble polymer of which the nitrogen atom can be protonated, and c) 0.001-0.5 wt %, based on the non surface-crosslinked water-absorbing polymer, of at least one hydrophobic polymer selected from the group consisting of a polyurethane, a poly(meth)acrylate, a polyacrylate, a copolymer of styrene-(meth)acrylate, a copolymer of styrene and (meth)acrylate comprising acrylonitrile, a copolymer of butadiene styrene and acrylonitrile, a (co)polymer of (crosslinkable) N-vinylpyrrolidone, and a (co)polymer of vinylacetate and heat-treating the resulting particles at a temperature in a range from 120° C. to 300° C.

2. The water-absorbing material according to claim 1, wherein less than 2% by weight of the non surface-crosslinked water-absorbing polymeric particles have a particle size of above 600 μm.

3. The water-absorbing material according to claim 1, wherein not less than 90% by weight of the non surface-crosslinked water-absorbing polymeric particles have a particle size in the range from 150 to 600 μm.

4. The water absorbing material according to claim 1, wherein the postcrosslinker is selected from the group consisting of amide acetals, carbamic esters, cyclic carbonic esters, bisoxazolines, polyhydric alcohols having a molecular weight of less than 100 g/mol per hydroxyl group, and mixtures thereof.

5. The water absorbing material according to claim 1, wherein the nitrogen atom-containing water-soluble polymer is selected from the group consisting of polyvinylamine and partially hydrolysed polyvinylformamide or polyvinylacetamide, polyallylamine, thermally stable derivatives of polyethyleneimine, and mixtures thereof.

6. The water-absorbing material according to claim 1, wherein the non surface-crosslinked water-absorbing polymer is brought in contact with
0.001-0.2 wt. % of at least one hydrophobic polymer, based on the non surface-crosslinked water-absorbing polymer.

7. The water-absorbing material according to claim 1 wherein the at least one hydrophobic polymer comprises a polyurethane.

8. The water-absorbing material according to claim 1 wherein the at least one hydrophobic polymer is non-reactive with the non-surface-crosslinked water-absorbing polymer.

9. The water-absorbing material according to claim 1 wherein the water-absorbing polymeric particles comprise in polymerized form
   i) at least one ethylenically unsaturated acid functional monomer, and
   ii) at least one crosslinker.

10. The water-absorbing material according to claim 9 wherein the water absorbing polymer particles further comprise in polymerized form
    iv) one or more water-soluble polymer grafted wholly or partly with monomers i) and ii).

11. The water-absorbing material according to claim 9 wherein the water absorbing polymer particles further comprise in polymerized form
    iii) one or more ethylenically and/or allylically unsaturated monomer copolymerizable with i).

12. The water-absorbing material according to claim 11 wherein the water absorbing polymer particles further comprise in polymerized form
    iv) one or more water-soluble polymer grafted wholly or partly with monomers i), ii), and iii).

* * * * *